United States Patent
Kurihara et al.

(10) Patent No.: US 9,868,906 B2
(45) Date of Patent: *Jan. 16, 2018

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Eriko Kurihara, Chiba (JP); Masayuki Saito, Chiba (JP); Yoshimasa Furusato, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/908,547

(22) PCT Filed: Jun. 19, 2014

(86) PCT No.: PCT/JP2014/066292
§ 371 (c)(1),
(2) Date: Jan. 29, 2016

(87) PCT Pub. No.: WO2015/025604
PCT Pub. Date: Feb. 26, 2015

(65) Prior Publication Data
US 2016/0168463 A1  Jun. 16, 2016

(30) Foreign Application Priority Data

Aug. 20, 2013 (JP) ................... 2013-170203

(51) Int. Cl.
| | |
|---|---|
| C07C 43/29 | (2006.01) |
| C09K 19/34 | (2006.01) |
| C09K 19/12 | (2006.01) |
| C09K 19/54 | (2006.01) |
| C09K 19/30 | (2006.01) |
| C09K 19/42 | (2006.01) |
| C07C 25/18 | (2006.01) |
| C07D 309/06 | (2006.01) |
| C09K 19/04 | (2006.01) |

(52) U.S. Cl.
CPC .......... *C09K 19/3402* (2013.01); *C07C 25/18* (2013.01); *C07D 309/06* (2013.01); *C09K 19/12* (2013.01); *C09K 19/3003* (2013.01); *C09K 19/3066* (2013.01); *C09K 19/42* (2013.01); *C09K 19/54* (2013.01); *C09K 19/542* (2013.01); *C09K 2019/0448* (2013.01); *C09K 2019/124* (2013.01); *C09K 2019/125* (2013.01); *C09K 2019/3025* (2013.01); *C09K 2019/3422* (2013.01); *C09K 2019/3425* (2013.01); *C09K 2019/548* (2013.01)

(58) Field of Classification Search
CPC .................................................... C09K 19/12
See application file for complete search history.

(56) References Cited

U.S. PATENT DOCUMENTS

| | | | | |
|---|---|---|---|---|
| 7,125,589 | B1 * | 10/2006 | Kimura | C07C 17/263 252/299.61 |
| 2006/0263544 | A1 * | 11/2006 | Klasen-Memmer | C09K 19/12 428/1.1 |
| 2012/0119141 | A1 | 5/2012 | Manabe | |
| 2012/0162595 | A1 | 6/2012 | Lee | |
| 2013/0314655 | A1 * | 11/2013 | Archetti | C09K 19/3003 349/124 |

FOREIGN PATENT DOCUMENTS

| | | |
|---|---|---|
| DE | 102010025572 | 1/2012 |
| JP | 2003-301179 | 10/2003 |
| JP | 2004-002341 | 1/2004 |
| WO | 2011009524 | 1/2011 |
| WO | 2011029510 | 3/2011 |

OTHER PUBLICATIONS

"International Search Report (Form PCT/ISA/210)", dated Sep. 22, 2014, pp. 1-4, with English translation thereof.

* cited by examiner

*Primary Examiner* — Chanceity Robinson
(74) *Attorney, Agent, or Firm* — JCIPRNET

(57) ABSTRACT

A liquid crystal composition satisfies at least one of characteristics such as a high maximum temperature of a nematic phase, a low minimum temperature of the nematic phase, small viscosity, suitable optical anisotropy, large negative dielectric anisotropy, large specific resistance, high stability to ultraviolet light and heat, or has a suitable balance regarding at least two of the characteristics. The composition contains a specific compound having high stability to ultraviolet light as a first component, and a liquid crystal display device includes the composition. The composition may contain a specific compound having large negative dielectric anisotropy as a second component, a specific compound having high maximum temperature or small viscosity as a third component, and a specific compound having a polymerizable group as an additive component.

18 Claims, No Drawings

LIQUID CRYSTAL COMPOSITION AND LIQUID CRYSTAL DISPLAY DEVICE

CROSS-REFERENCE TO RELATED APPLICATION

This application is a 371 application of International PCT application serial no. PCT/JP2014/066292, filed on Jun. 19, 2014, which claims the priority benefit of Japan application serial no. 2013-170203, filed on Aug. 20, 2013. The entirety of each of the above-mentioned patent applications is hereby incorporated by reference herein and made a part of this specification.

TECHNICAL FIELD

The invention relates to a liquid crystal composition, a liquid crystal display device including the composition, and so forth. In particular, the invention relates to a liquid crystal composition having a negative dielectric anisotropy, and a liquid crystal display device that includes the composition and has a mode such as an IPS mode, a VA mode, an FFS mode and an FPA mode. The invention also relates to a liquid crystal display device having a polymer sustained alignment mode.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static and multiplex and so forth. The AM is classified into a thin film transistor (TFT), a metal insulator metal (MIM) and so forth. The TFT is further classified into amorphous silicon and polycrystal silicon based on a material. The latter is further classified into a high temperature type and a low temperature type based on a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the liquid crystal composition relates to a response time of the device. A short response time is preferred for displaying moving images on the device. A shorter response time even by one millisecond is desirable. Accordingly, a small viscosity of the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |

[1] A liquid crystal composition can be injected into a liquid crystal display device in a short time.

An optical anisotropy of the composition relates to a contrast ratio in the device. According to a mode of the device, a large optical anisotropy or a small optical anisotropy, more specifically, a suitable optical anisotropy is required. A product (Δn×d) of the optical anisotropy (Δn) of the composition and a cell gap (d) in the device is designed so as to maximize the contrast ratio. A suitable value of the product depends on a type of the operating mode. The suitable value is in the range of about 0.30 micrometer to about 0.40 micrometer in a device having the VA mode, and is in the range of about 0.20 micrometer to about 0.30 micrometer in a device having the IPS mode or the FFS mode. In the above cases, a composition having the large optical anisotropy is preferred for a device having a small cell gap. A large dielectric anisotropy in the composition contributes to a low threshold voltage, a small electric power consumption and a large contrast ratio in the device. Accordingly, the large dielectric anisotropy is preferred. A large specific resistance in the composition contributes to a large voltage holding ratio and the large contrast ratio in the device. Accordingly, a composition having the large specific resistance at room temperature and also at a high temperature in an initial stage is preferred. The composition having the large specific resistance at room temperature and also at a high temperature after the device has been used for a long period of time is preferred. Stability of the composition to ultraviolet light and heat relates to a service life of the device. In the case where the stability is high, the device has a long service life. Such characteristics are preferred for an AM device used in a liquid crystal projector, a liquid crystal television and so forth.

In a liquid crystal display device having a polymer sustained alignment (PSA) mode, a liquid crystal composition containing a polymer is used. First, a composition to which a small amount of polymerizable compound is added is injected into the device. Then, the composition is irradiated with ultraviolet light while voltage is applied between substrates of the device. The polymerizable compound is polymerized to form a network structure of the polymer in the liquid crystal composition. In the composition, alignment of liquid crystal molecules can be controlled by the polymer, and therefore the response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

A composition having a positive dielectric anisotropy is used in an AM device having the TN mode. In an AM device having the VA mode, a composition having a negative dielectric anisotropy is used. A composition having the positive or negative dielectric anisotropy is used in an AM device having the IPS mode or the FFS mode. In an AM device of the polymer sustained alignment mode, a composition having the positive or negative dielectric anisotropy is used. An example of a liquid crystal composition relates to the invention is disclosed in Patent literature Nos. 1 and 2. An example of a composition for a device having the polymer sustained alignment (PSA) mode is disclosed in Patent literature No. 3.

CITATION LIST

Patent Literature

Patent literature No. 1: DE 102010025572A1 B.
Patent literature No. 2: WO 2011-009524 A.
Patent literature No. 3: WO 2011-029510 A.

SUMMARY OF THE INVENTION

Technical Problem

One of the aims of the invention is to provide a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. Another aim is to provide a liquid crystal composition having a suitable balance regarding at least two of the characteristics. Another aim is to provide a liquid crystal display device including such a composition. Another aim is to provide an AM device having characteristics such as a short response time, a large voltage holding ratio, a low threshold voltage, a large contrast ratio and a long service life.

Solution to Problem

The invention concerns a liquid crystal composition that has a negative dielectric anisotropy and contains at least one compound selected from the group of compounds represented by formula (1) as a first component, and concerns a liquid crystal display device including the composition:

$Z^1$, $Z^2$, $Z^3$ and $Z^4$ are independently a single bond, —CH$_2$CH$_2$—, —CH$_2$O—, —OCH$_2$—, —COO— or —OCO—; a, b and c are independently 0, 1, 2, 3 or 4; and d is 0, 1 or 2.

Advantageous Effects of Invention

An advantage of the invention is a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. Another advantage is a liquid crystal composition having a suitable balance regarding at least two of the characteristics. Another advantage is a liquid crystal display device including such a composition. Another advantage is an AM device having characteristics such as a short response time, a large voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but to be mixed with a composition for the purpose of adjusting characteristics such as a temperature range of the nematic phase, viscosity and dielectric anisotropy. The compound has a six-membered ring such as 1,4-cyclohexylene and 1,4-phenylene, and has rod like molecular structure. "Polymerizable compound" includes a compound to be added to the composition for the purpose of forming a polymer in the composition. At least one compound selected from the group of compounds represented by formula (1) may be occasionally abbreviated as "compound (1)." "Compound (1)" means one compound represented by formula (1), a mixture of two compounds, or

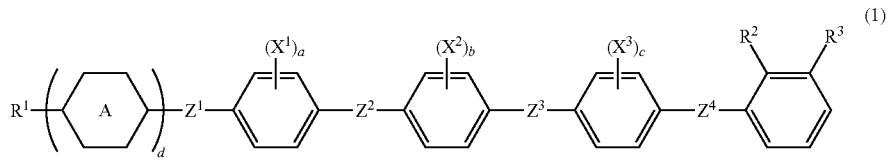

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, in which at least one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine or alkyl having 1 to 12 carbons in which at least one of hydrogen may be replaced by fluorine;

a mixture of three or more compounds. A same rule applies also to any other compound represented by any other formula.

The liquid crystal composition is prepared by mixing a plurality of liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, the polymerizable compound, a polymerization initiator and a polymerization inhibitor is added to the composition when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. A ratio of the polymerization initiator and the polymerization inhibitor is exceptionally expressed based on the weight of the polymerizable compound.

An expression "maximum temperature of the nematic phase" may be occasionally abbreviated as "maximum temperature." An expression "minimum temperature of the nematic phase" may be occasionally abbreviated as "minimum temperature." An expression "having a large specific resistance" means that the composition has a large specific resistance at room temperature and also at a temperature close to the maximum temperature of the nematic phase in an initial stage, and the composition has the large specific resistance at room temperature and also at a temperature close to the maximum temperature of the nematic phase even after the device has been used for a long period of time. An expression "having a large voltage holding ratio" means that the device has a large voltage holding ratio at room temperature and also at a temperature close to the maximum temperature of the nematic phase in the initial stage, and the device has the large voltage holding ratio at room temperature and also at a temperature close to the maximum temperature of the nematic phase even after the device has been used for the long period of time. An expression "increases the dielectric anisotropy" means that the value positively increases for the composition having a positive dielectric anisotropy, and that the value negatively increases for the composition having a negative dielectric anisotropy.

An expression "at least one of 'A' may be replaced by 'B'" means that the number of 'A' is arbitrary. When the number of 'A' is 1, a position of 'A' is arbitrary, and also when the number of 'A' is 2 or more, positions thereof can be selected without restriction. A same rule applies also to an expression "at least one of 'A' is replaced by 'B'."

A symbol of terminal group $R^1$ is used for a plurality of compounds in chemical formulas of component compounds. In the compounds, two groups represented by two of arbitrary $R^1$ may be identical or different. In one case, for example, $R^1$ of compound (1-1) is ethyl and $R^1$ of compound (1-2) is ethyl. In another case, for example, $R^1$ of compound (1-1) is ethyl and $R^1$ of compound (1-2) is propyl. A same rule applies also to a symbol of $R^3$ and $X^1$ or the like. In formula (2), when e is 2, two of ring B exist. In the compound, two rings represented by two of ring B may be identical or different. A same rule applies also to two of arbitrary ring B when e is larger than 2. A same rule applies also to a symbol of $Z^7$ and a ring E or the like.

In a phenylene ring in compound (1), a perpendicular line crossing a hexagonal shape means that a position can be arbitrarily selected in which hydrogen on the six-membered ring is replaced by a group such as $X^1$. A subscript such as a and b represent the number of groups subjected to replacement. In compound (4), a hexagonal shape represents a ring without being limited to the six-membered ring. An oblique line crossing the hexagonal shape means that arbitrary hydrogen on the ring may be replaced by a group such as $P^1$-$Sp^1$. A subscript such as j represents the number of groups subjected to replacement.

Then, 2-fluoro-1,4-phenylene means two divalent groups described below. In a chemical formula, fluorine may be leftward (L) or rightward (R). A same rule applies also to a divalent group of asymmetrical ring such as tetrahydropyran-2,5-diyl.

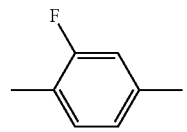

(L)

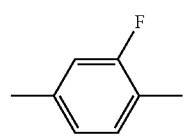

(R)

The invention includes the items described below.

Item 1. A liquid crystal composition that has a negative dielectric anisotropy, and contains at least one compound selected from the group of compounds represented by formula (1) as a first component:

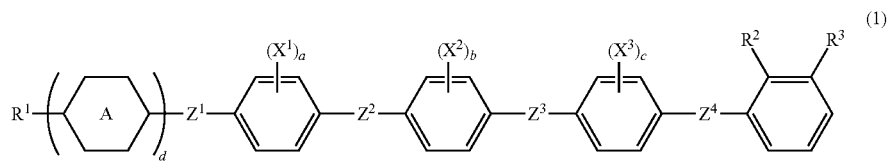

(1)

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, in which at least one of $R^2$ and $R^3$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; $Z^1$, $Z^2$, $Z^3$ and $Z^4$ are independently a single bond, —CH$_2$CH$_2$—, —CH$_2$O—, —OCH$_2$—, —COO— or —OCO—; a, b and c are independently 0, 1, 2, 3 or 4; and d is 0, 1 or 2.

Item 2. The liquid crystal composition according to item 1, containing at least one compound selected from the group of compounds represented by formulas (1-1) to (1-3) as the first component:

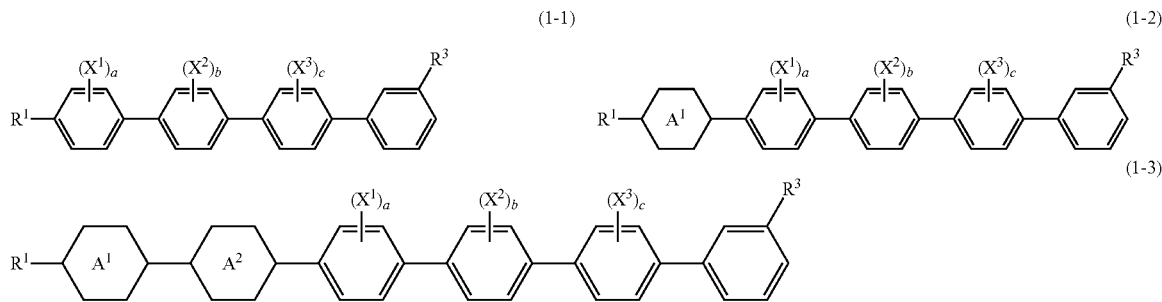

wherein, in formula (1-1) to formula (1-3), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; rings $A^1$ and $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; and a, b and c are independently 0, 1, 2, 3 or 4.

Item 3. The liquid crystal composition according to item 1 or 2, containing at least one compound selected from the group of compounds represented by formulas (1-1-1) to (1-1-9), formula (1-2-1) and formula (1-2-2) as the first component:

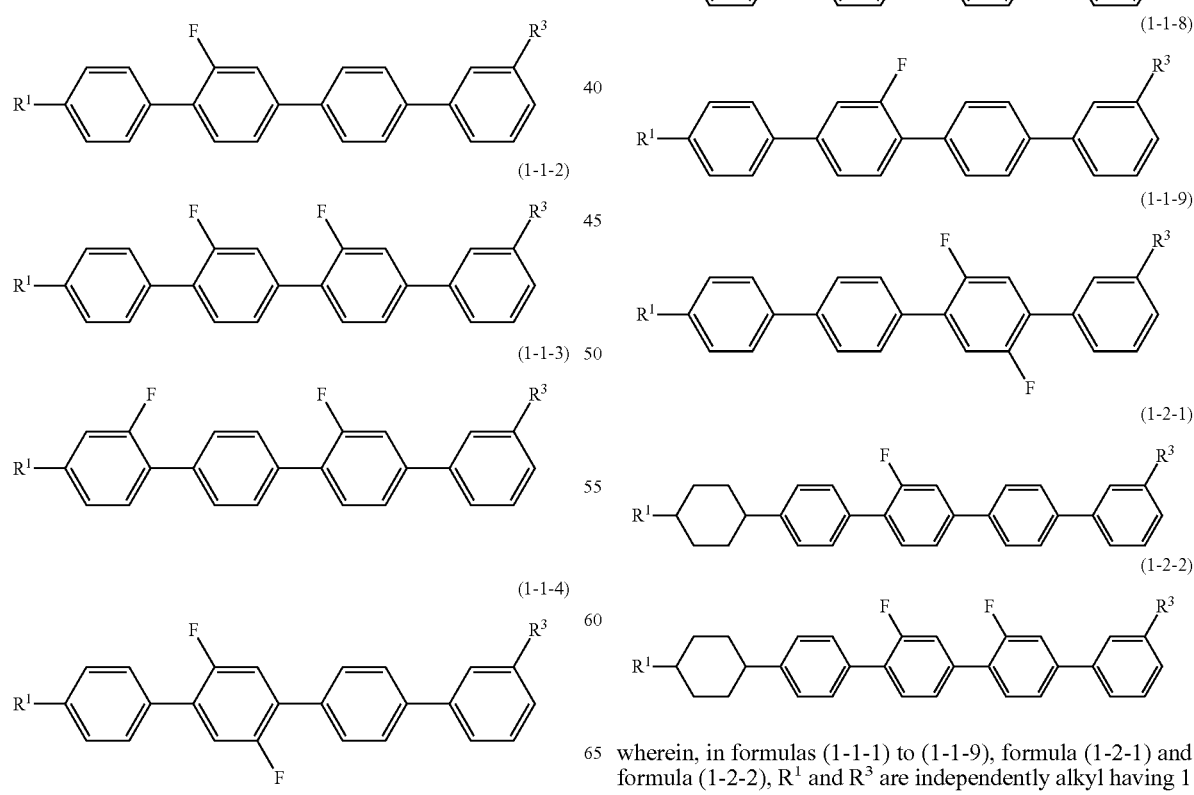

wherein, in formulas (1-1-1) to (1-1-9), formula (1-2-1) and formula (1-2-2), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 4. The liquid crystal composition according to any one of items 1 to 3, wherein a ratio of the first component is in the range of 0.03% by weight to 10% by weight based on the weight of the liquid crystal composition.

Item 5. The liquid crystal composition according to any one of items 1 to 4, containing at least one compound selected from the group of compounds represented by formula (2) as a second component:

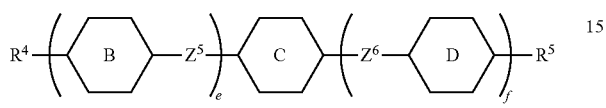
(2)

wherein, in formula (2), $R^4$ and $R^5$ are independently alkyl having 1 to 12 carbons, alkoxy having 1 to 12 carbons, alkenyl having 2 to 12 carbons or alkenyloxy having 2 to 12 carbons; ring B and ring D are independently 1,4-cyclohexylene, 1,4-cyclohexenylene, 1,4-phenylene, 1,4-phenylene in which at least one of hydrogen is replaced by fluorine or chlorine, or tetrahydropyran-2,5-diyl; ring C is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^5$ and $Z^6$ are independently a single bond, —CH$_2$CH$_2$—, —CH$_2$O—, —OCH$_2$—, —COO— or —OCO—; and e is 1, 2 or 3, f is 0 or 1 and a sum of e and f is 3 or less.

Item 6. The liquid crystal composition according to any one of items 1 to 5, containing at least one compound selected from the group of compounds represented by formulas (2-1) to (2-19) as the second component:

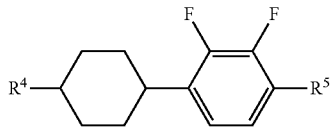
(2-1)

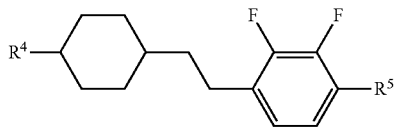
(2-2)

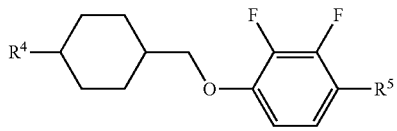
(2-3)

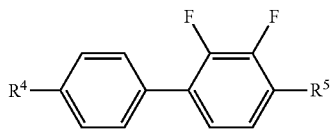
(2-4)

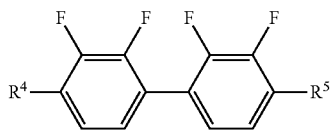
(2-5)

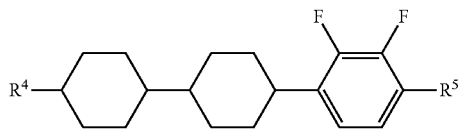
(2-6)

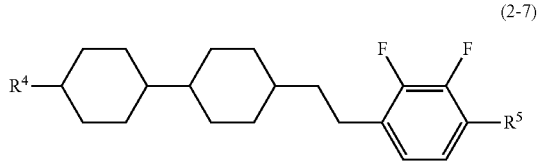
(2-7)

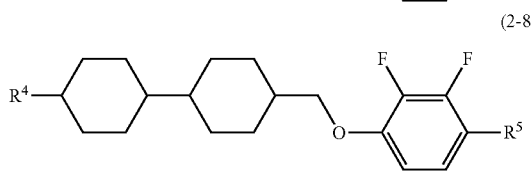
(2-8)

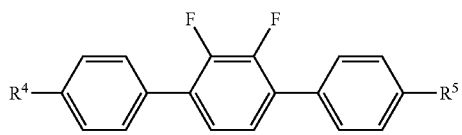
(2-9)

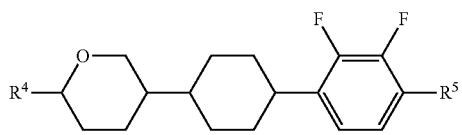
(2-10)

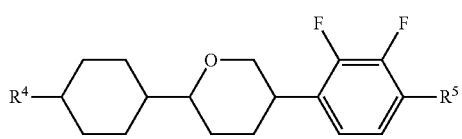
(2-11)

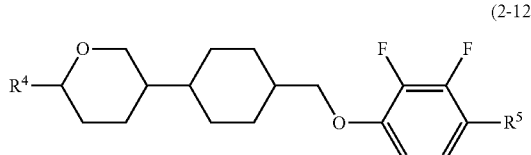
(2-12)

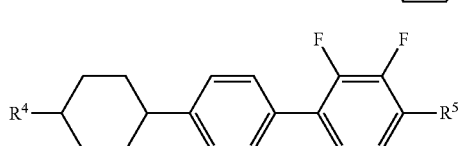
(2-13)

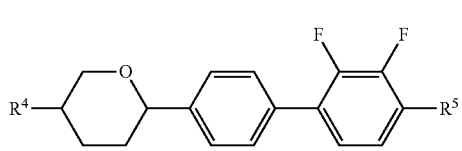
(2-14)

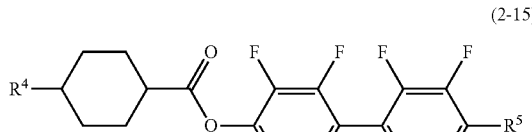
(2-15)

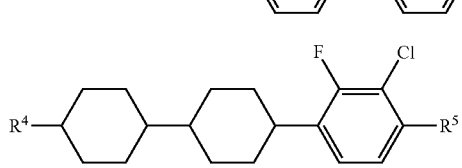
(2-16)

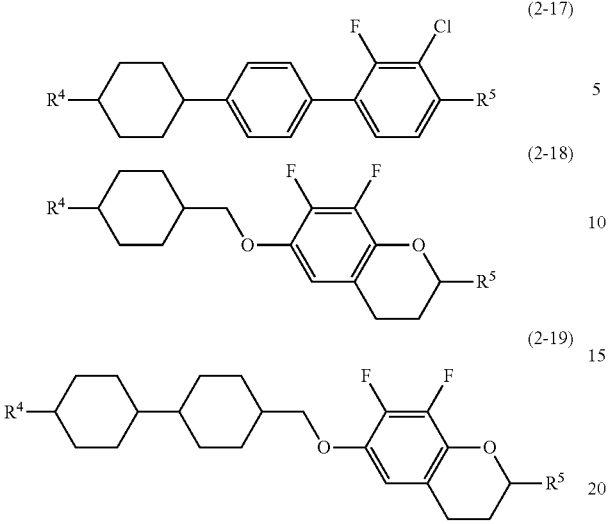

wherein, in formula (2-1) to formula (2-19), $R^4$ and $R^5$ are independently alkyl having 1 to 12 carbons, alkoxy having 1 to 12 carbons, alkenyl having 2 to 12 carbons or alkenyloxy having 2 to 12 carbons.

Item 7. The liquid crystal composition according to item 5 or 6, wherein a ratio of the second component is in the range of 10% by weight to 90% by weight based on the weight of the liquid crystal composition.

Item 8. The liquid crystal composition according to any one of items 1 to 7, further containing at least one compound selected from the group of compounds represented by formula (3) as a third component:

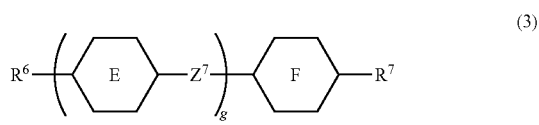

wherein, in formula (3), $R^6$ and $R^7$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring E and ring F are independently 1,4-cyclohexylene, 1,4-phenylene, 2-fluoro-1,4-phenylene or 2,5-difluoro-1,4-phenylene; $Z^7$ is a single bond, —CH$_2$CH$_2$—, —CH$_2$O—, —OCH$_2$—, —OCO— or —OCO—; and g is 1, 2 or 3.

Item 9. The liquid crystal composition according to any one of items 1 to 8, containing at least one compound selected from the group of compounds represented by formulas (3-1) to (3-13) as the third component:

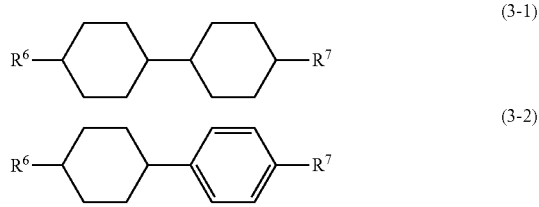

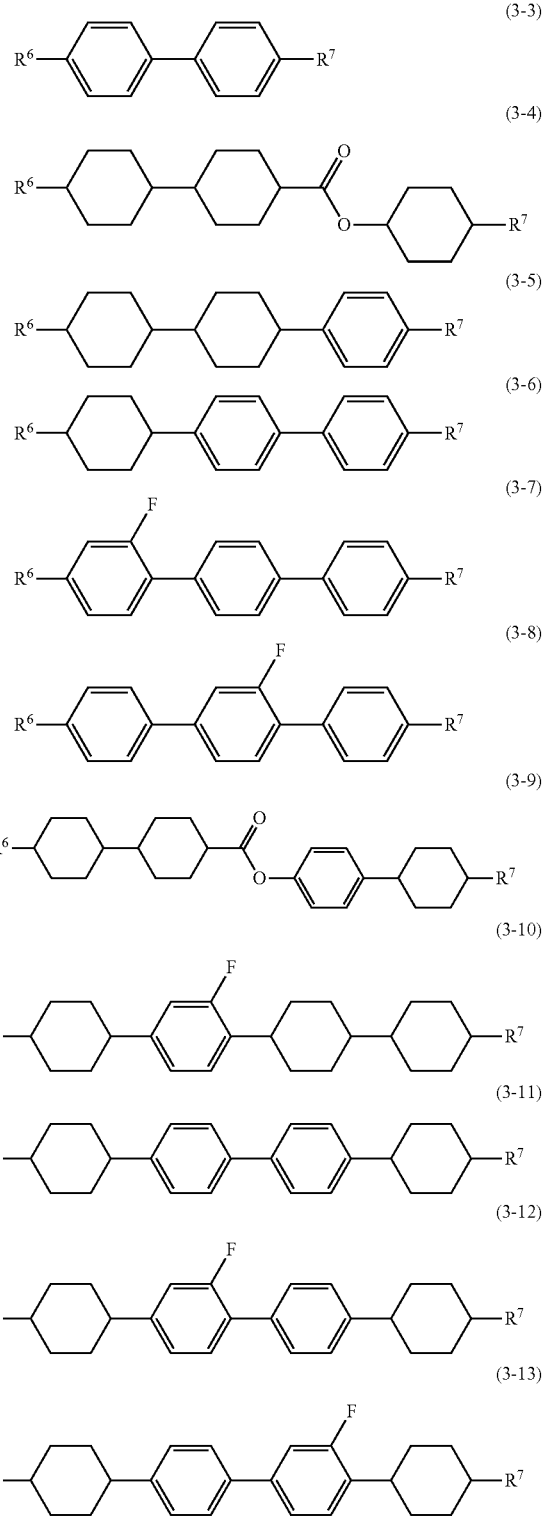

wherein, in formula (3-1) to formula (3-13), $R^6$ and $R^7$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 10. The liquid crystal composition according to item 8 or 9, wherein a ratio of the third component is in the range of 10% by weight to 90% by weight based on the weight of the liquid crystal composition.

Item 11. The liquid crystal composition according to any one of items 1 to 10, containing at least one polymerizable compound selected from the group of compounds represented by formula (4) as an additive component:

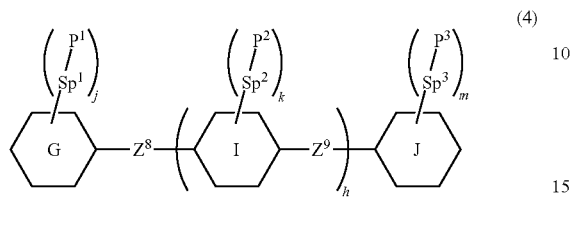

(4)

wherein, in formula (4), ring G and ring J are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; ring I is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; $Z^8$ and $Z^9$ are independently a single bond or alkylene having 1 to 10 carbons, and in the alkylene, at least one of —$CH_2$— may be replaced by —O—, —CO—, —OCO— or —OCO—, and at least one of —$CH_2$—$CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine; $P^1$, $P^2$ and $P^3$ are a polymerizable group; $Sp^1$, $Sp^2$ and $Sp^3$ are independently a single bond or alkylene having 1 to 10 carbons, and in the alkylene, at least one of —$CH_2$— may be replaced by —O—, —OCO—, —OCO— or —OCOO—, and at least one of —$CH_2$—$CH_2$— may be replaced by —CH=CH— or —C≡C—, and in the groups, at least one of hydrogen may be replaced by fluorine or chlorine; h is 0, 1 or 2; and j, k and m are independently 0, 1, 2, 3 or 4, and a sum of j, k and m is 1 or more.

Item 12. The liquid crystal composition according to item 11, wherein, in formula (4) described in item 11, $P^1$, $P^2$ and $P^3$ are independently a polymerizable group selected from the group of groups represented by formulas (P-1) to (P-5):

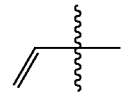

(P-1)

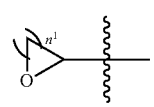

(P-2)

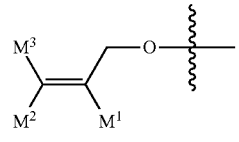

(P-3)

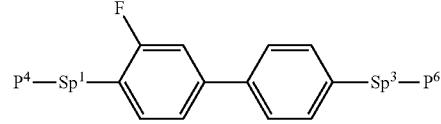

(P-4)

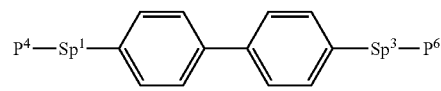

(P-5)

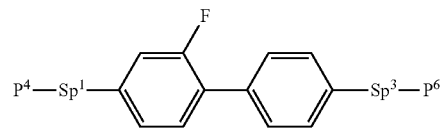

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (P-5), $n^1$ is 1, 2, 3 or 4; when both $P^1$ and $P^3$ are a group represented by formula (P-4), at least one of $Sp^1$ and $Sp^3$ is alkylene in which at least one of —$CH_2$— is replaced by —O—, —OCO—, —OCO— or —OCOO—.

Item 13. The liquid crystal composition according to any one of items 1 to 12, containing at least one polymerizable compound selected from the group of compounds represented by formulas (4-1) to (4-27) as the additive component:

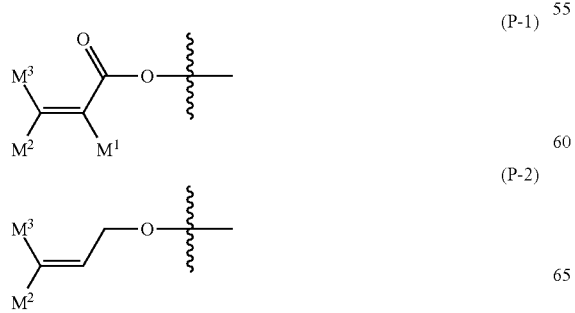

(4-1)

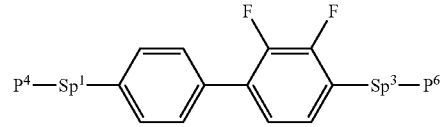

(4-2)

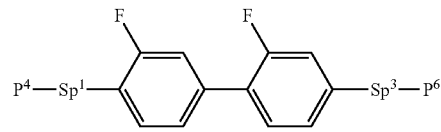

(4-3)

(4-4)

(4-5)

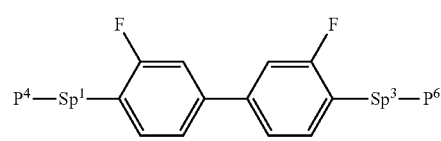

(4-6)

(4-7) 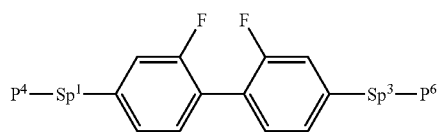
(4-8) 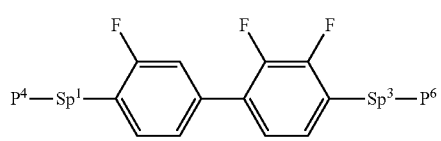
(4-9) 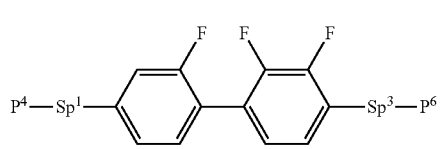
(4-10) 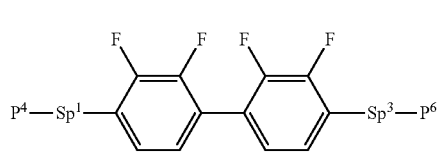
(4-11) 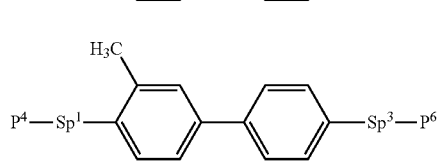
(4-12) 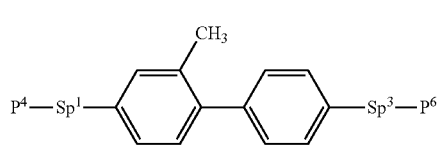
(4-13) 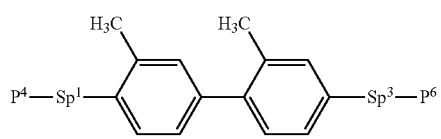
(4-14) 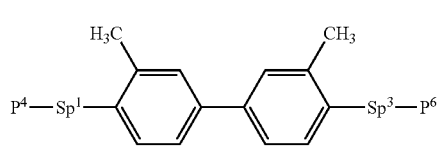
(4-15) 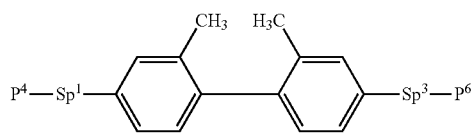
(4-16) 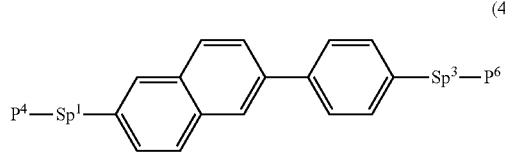
(4-17) 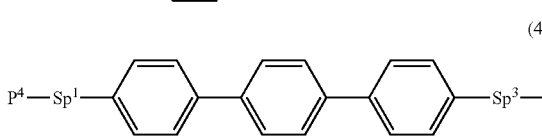
(4-18) 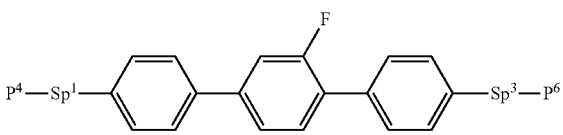
(4-19) 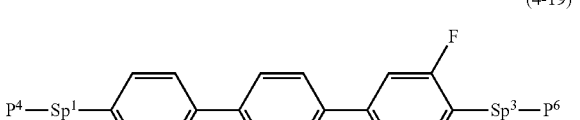
(4-20) 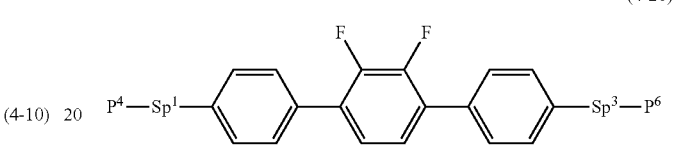
(4-21) 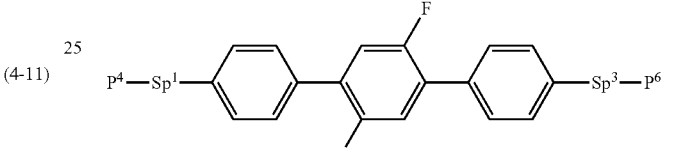
(4-22) 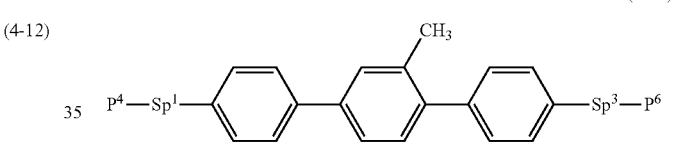
(4-23) 
(4-24) 
(4-25) 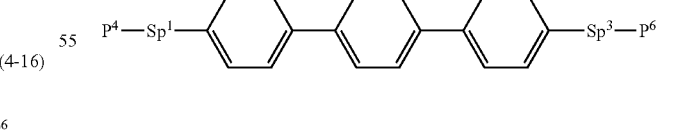
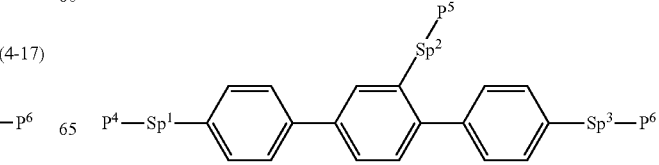

(4-26)

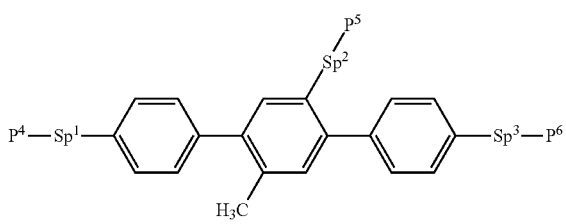

(4-27)

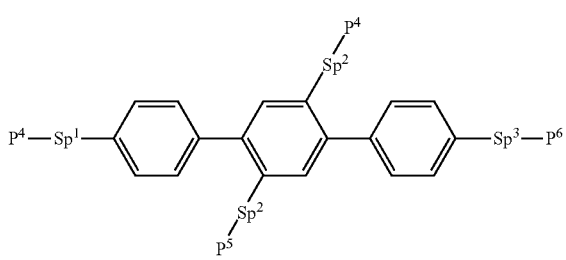

wherein, in formula (4-1) to formula (4-27), $P^4$, $P^5$ and $P^6$ are independently a group represented by formulas (P-1) to (P-3);

(P-1)

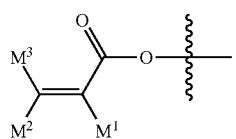

(P-2)

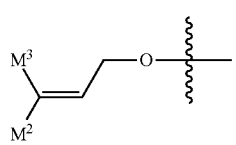

(P-3)

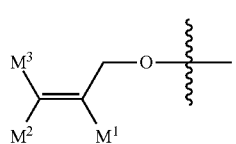

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (4-1) to formula (4-27), $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$—CH$_2$— may be replaced by —CH=CH— or —C≡C—, and in the groups, at least one of hydrogen may be replaced by fluorine or chlorine.

Item 14. The liquid crystal composition according to any one of items 11 to 13, wherein a ratio of addition of the additive component is in the range of 0.03% by weight to 10% by weight, based on the weight of the liquid crystal composition before adding an additive thereto.

Item 15. A liquid crystal display device, including the liquid crystal composition according to any one of items 1 to 14.

Item 16. The liquid crystal display device according to item 15, wherein an operating mode in the liquid crystal display device is an IPS mode, a VA mode, an FFS mode or an FPA mode, and a driving mode in the liquid crystal display device is an active matrix mode.

Item 17. A polymer sustained alignment mode liquid crystal display device, wherein the liquid crystal display device includes the liquid crystal composition according to any one of items 11 to 14, and a polymerizable compound in the composition is polymerized.

Item 18. Use of the liquid crystal composition according to any one of items 1 to 14 in a liquid crystal display device.

Item 19. Use of the liquid crystal composition according to any one of items 11 to 14 in a polymer sustained alignment mode liquid crystal display device.

The invention further includes the following items: (c) the composition containing at least one compound selected from the group of compound (5) to compound (7) having a positive dielectric anisotropy as described in JP 2006-199941 A; (d) the composition containing polymerizable compound (4); (e) the composition containing a polymerizable compound different from polymerizable compound (4); (f) the composition, containing at least one of additives such as an optically active compound, an antioxidant, an ultraviolet light absorber, a dye, an antifoaming agent, a polymerization initiator or a polymerization inhibitor; (g) an AM device including the composition; (h) a device including the composition and having the TN mode, the ECB mode, the OCB mode, the IPS mode, the FFS mode, the VA mode or the FPA mode; (i) a transmissive device including the composition; (j) use of the composition as the composition having the nematic phase; and (k) use as an optically active composition by adding the optically active compound to the composition.

The composition of the invention will be described in the following order. First, a constitution of the component compounds in the composition will be described. Second, main characteristics of the component compounds and main effects of the compounds on the composition will be described. Third, a combination of components in the composition, a preferred ratio of the components and the basis thereof will be described. Fourth, a preferred embodiment of the component compounds will be described. Fifth, a preferred component compounds will be shown. Sixth, an additive that may be added to the composition will be described. Seventh, methods for synthesizing the component compounds will be described. Last, an application of the composition will be described.

First, the constitution of the component compounds in the composition will be described. The composition of the invention is classified into composition A and composition B. Composition A may further contain any other liquid crystal compound, any other additive or the like in addition to the liquid crystal compound selected from compound (1), compound (2) and compound (3), and compound (4). "Any other liquid crystal compound" means a liquid crystal compound different from compound (1), compound (2), compound (3) and compound (4). Such a compound is mixed with the composition for the purpose of further adjusting the characteristics. Of other liquid crystal compounds, a ratio of a cyano compound is preferably as small as possible in view of stability to heat or ultraviolet light. A further preferred ratio of the cyano compound is 0% by weight. The additive is the optically active compound, the antioxidant, the ultraviolet light absorber, the dye, the antifoaming agent, the polymerizable compound, the polymerization initiator, the polymerization inhibitor or the like.

Composition B consists essentially of liquid crystal compounds selected from compound (1), compound (2), compound (3) and compound (4). "Essentially" means that the composition may contain any other additive, but contains no compound different from compound (1), compound (2), compound (3) and compound (4). Composition B has a smaller number of components than composition A has. Composition B is preferred to composition A in view of cost reduction. Composition A is preferred to composition B in view of possibility of further adjusting the characteristics by mixing any other liquid crystal compound.

Second, the main characteristics of the component compounds and the main effects of the compounds on the characteristics of the composition will be described. The main characteristics of the component compounds are summarized in Table 2 on the basis of advantageous effects of the invention. In Table 2, a symbol L stands for "large" or "high," a symbol M stands for "medium" and a symbol S stands for "small" or "low." The symbols L, M and S represent a classification based on a qualitative comparison among the component compounds, and 0 (zero) means "a value is nearly zero."

TABLE 2

Characteristics of Compounds

| Compounds | (1) | (2) | (3) |
|---|---|---|---|
| Maximum temperature | L | S to L | S to L |
| Viscosity | M to L | M to L | S to M |
| Optical anisotropy | L | M to L | S to L |
| Dielectric anisotropy | 0 | S to L[1)] | 0 |
| Specific resistance | L | L | L |

[1)]A value of dielectric anisotropy is negative, and the symbol shows magnitude of an absolute value.

Upon mixing the component compounds with the composition, the main effects of the component compounds on the characteristics of the composition are as described below. Compound (1) maintains a high stability to ultraviolet light. Compound (2) increases the dielectric anisotropy and decreases a minimum temperature. Compound (3) decreases the viscosity or increases the maximum temperature. Compound (4) is polymerized to give a polymer, and the polymer shortens a response time of the device, and improves image persistence.

Third, the combination of components in the composition, the preferred ratio of the components and the basis thereof will be described. The combination of components in the composition includes a combination of the first component and the second component, a combination of the first component, the second component and the third component, a combination of the first component, the second component and the additive component, and a combination of the first component, the second component, the third component and the additive component. A preferred combination of components includes a combination of the first component, the second component and the third component, or a combination of the first component, the second component, the third component and the additive component. Wherein, the additive component means polymerizable compound (4).

A preferred ratio of the first component is about 0.03% by weight or more for maintaining the high stability to ultraviolet light, and about 10% by weight or less for decreasing the minimum temperature, based on the weight of the liquid crystal composition. A further preferred ratio is in the range of about 0.1% by weight to about 2% by weight. A particularly preferred ratio is in the range of about 0.3% by weight to about 1.5% by weight.

A preferred ratio of the second component is about 10% by weight or more for increasing the dielectric anisotropy, and about 90% by weight or less for decreasing the viscosity, based on the weight of the liquid crystal composition. A further preferred ratio is in the range of about 20% by weight to about 80% by weight. A particularly preferred ratio is in the range of about 30% by weight to about 70% by weight.

A preferred ratio of the third component is about 10% by weight or more for increasing the maximum temperature or decreasing the viscosity, and about 90% by weight or less for decreasing the minimum temperature, based on the weight of the liquid crystal composition. A further preferred ratio is in the range of about 20% by weight to about 80% by weight. A particularly preferred ratio is in the range of about 30% by weight to about 70% by weight.

Compound (4) is added to the composition for the purpose of adapting the composition for the polymer sustained alignment mode device. A preferred ratio of addition of the additive is about 0.03% by weight or more for aligning the liquid crystal molecules, and about 10% by weight or less for preventing poor display in the device, based on the weight of the liquid crystal composition before adding the additive thereto. A further preferred ratio of addition is in the range of about 0.1% by weight to about 2% by weight. A particularly preferred ratio of addition is in the range of about 0.2% by weight to about 1% by weight.

The characteristics of the composition described in Table 1 can be adjusted by adjusting the ratio of the component compounds. The characteristics of the composition may be adjusted by mixing any other liquid crystal compound when necessary. A composition having a maximum temperature of about 70° C. or higher can be prepared by such a method. A composition having a maximum temperature of about 75° C. or higher can also be prepared. A composition having a maximum temperature of about 80° C. or higher can also be prepared. A composition having a minimum temperature of about −10° C. or lower can be prepared by such a method. A composition having a minimum temperature of about −20° C. or lower can also be prepared. A composition having a minimum temperature of about −30° C. or lower can also be prepared.

A composition having optical anisotropy (measured at 25° C.) at a wavelength of 589 nanometers in the range of about 0.09 to about 0.12 can be prepared by such a method. A composition having optical anisotropy in the range of about 0.08 to about 0.16 can also be prepared. A composition having optical anisotropy in the range of about 0.07 to about 0.20 can also be prepared. A composition having dielectric anisotropy (measured at 25° C.) of about −1.5 or less at a frequency of 1 kHz can be prepared by such a method. A composition having dielectric anisotropy of about −2 or less can also be prepared. A composition having dielectric anisotropy of about −2.5 or less can also be prepared.

Fourth, the preferred embodiment of the component compounds will be described. In compound (1) to compound (3), $R^1$, $R^2$, $R^3$, $R^6$ and $R^7$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, in which at least one of $R^2$ and $R^3$ may be hydrogen. Preferred $R^1$, $R^2$ or $R^3$ is alkyl having 1 to 12 carbons for increasing the stability to ultraviolet light or heat, and alkenyl having 2 to 12 carbons for decreasing the minimum temperature. Preferred $R^6$ or $R^7$ is alkyl having 1 to 12 carbons for increasing the stability to ultraviolet light or heat, and alkenyl having 2 to 12 carbons for decreasing the minimum temperature or decreasing the viscosity. $R^4$ and $R^5$ are independently alkyl having 1 to 12 carbons, alkoxy having 1 to 12 carbons, alkenyl having 2 to 12 carbons or alkenyloxy having 2 to 12 carbons. Preferred $R^6$ or $R^7$ is alkyl having 1 to 12 carbons for increasing the stability to ultraviolet light or heat, and alkoxy having 1 to 12 carbons for increasing the dielectric anisotropy.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in the alkenyl depends on a position of a double bond. Trans is preferred in alkenyl such as 1-propenyl, 1-butenyl, 1-pentenyl, 1-hexenyl, 3-pentenyl and 3-hexenyl for decreasing the viscosity, for instance. Cis is preferred in alkenyl such as 2-butenyl, 2-pentenyl and 2-hexenyl. In the alkenyl, straight-chain alkenyl is preferred to branched-chain alkenyl.

Preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Alkyl is straight-chain alkyl or branched-chain alkyl, but includes no cyclic alkyl. Straight-chain alkyl is preferred to branched-chain alkyl. A same rule applies also to alkoxy, alkenyl and alkenyl in which at least one of hydrogen is replaced by fluorine. With regard to a configuration of 1,4-cyclohexylene, trans is preferred to cis for increasing the maximum temperature.

Ring A, ring $A^1$ and ring $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl. Preferred ring A, ring $A^1$ or ring $A^2$ is 1,4-cyclohexylene for decreasing the minimum temperature.

Ring C is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Preferred ring C is 2,3-difluoro-1,4-phenylene for decreasing the viscosity, 2-chloro-3-fluoro-1,4-phenylene for decreasing the optical anisotropy, and 7,8-difluorochroman-2,6-diyl for increasing the dielectric anisotropy. Ring B and ring D are independently 1,4-cyclohexylene, 1,4-cyclohexenylene, 1,4-phenylene, 1,4-phenylene in which at least one of hydrogen is replaced by fluorine or chlorine or tetrahydropyran-2,5-diyl. Preferred ring B or ring D is 1,4-cyclohexylene for decreasing the viscosity, tetrahydropyran-2,5-diyl for increasing the dielectric anisotropy, and 1,4-phenylene for increasing the optical anisotropy. With regard to the configuration of 1,4-cyclohexylene, trans is preferred to cis for increasing the maximum temperature. Tetrahydropyran-2,5-diyl includes:

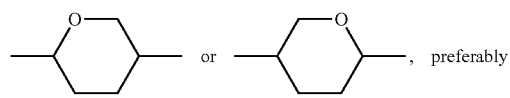, preferably

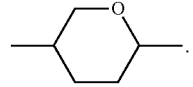

Ring E and ring F are independently 1,4-cyclohexylene, 1,4-phenylene, 2-fluoro-1,4-phenylene or 2,5-difluoro-1,4-phenylene. Preferred ring E or ring F is 1,4-cyclohexylene for decreasing the viscosity or increasing the maximum temperature, and 1,4-phenylene for decreasing the minimum temperature.

$X^1$, $X^2$ and $X^3$ are independently fluorine, chlorine, or alkyl having 1 to 12 carbons in which at least one of hydrogen may be replaced by fluorine. Preferred $X^1$, $X^2$ or $X^3$ is fluorine for decreasing the minimum temperature.

$Z^1$, $Z^2$, $Z^3$, $Z^4$ and $Z^7$ are independently a single bond, —CH$_2$CH$_2$—, —CH$_2$O—, —OCH$_2$—, —OCO— or —OCO—. Preferred $Z^1$, $Z^2$, $Z^3$ and $Z^4$ are a single bond for increasing the stability. Preferred $Z^7$ is a single bond for decreasing the viscosity. $Z^5$ and $Z^6$ are independently a single bond, —CH$_2$CH$_2$—, —CH$_2$O—, —OCH$_2$—, —COO— or —OCO—. Preferred $Z^5$ or $Z^6$ is a single bond for decreasing the viscosity, —CH$_2$CH$_2$— for decreasing the minimum temperature, and —CH$_2$O— for increasing the dielectric anisotropy.

Then, a, b and c are independently 0, 1, 2, 3 or 4. Preferred a, b or c is 1 or 2 for decreasing the minimum temperature, and 0 for increasing the maximum temperature. Then, d is independently 0, 1 or 2. Preferred d is 0 for decreasing the minimum temperature. Then, e is 1, 2 or 3, f is 0 or 1, and a sum of e and f is 3 or less. Preferred e is 1 for decreasing the viscosity, and 2 or 3 for increasing the maximum temperature. Preferred f is 0 for decreasing the viscosity, and 1 for decreasing the minimum temperature. Then, g is 1, 2 or 3. Preferred g is 2 for increasing the maximum temperature.

In compound (4), $P^1$, $P^2$ and $P^3$ are independently a polymerizable group. Preferred $P^1$, $P^2$ or $P^3$ is a polymerizable group selected from the group of groups represented by formulas (P-1) to (P-5). Preferred $P^1$, $P^2$ or $P^3$ is group (P-1) and group (P-2). Further preferred group (P-1) is —OCO—CH═CH$_2$ and —OCO—C(CH$_3$)═CH$_2$. A wavy line from group (P-1) to group (P-5) shows a site to be bonded.

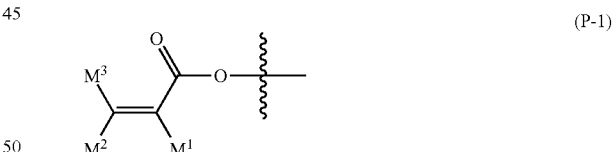
(P-1)

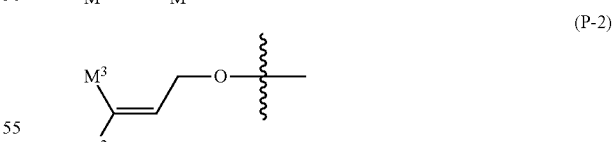
(P-2)

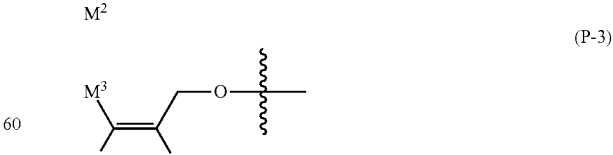
(P-3)

(P-4)

-continued

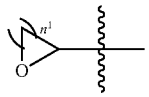
(P-5)

When all of $P^1$, $P^2$ and $P^3$ are group (P-1), $M^1$ (or $M^2$, or $M^3$) of $P^1$, $M^1$ of $P^2$ or $M^1$ of $P^3$ may be identical or different. In group (P-1), $M^1$, $M^2$ and $M^3$ are independently hydrogen, fluorine, alkyl having 1 to 5 carbons, or alkyl having 1 to 5 carbons in which at least one of hydrogen is replaced by halogen. Preferred $M^1$, $M^2$ or $M^3$ is hydrogen or methyl for increasing a reactivity. Further preferred $M^1$ is methyl, and further preferred $M^2$ or $M^3$ is hydrogen. In group (P-5), $n^1$ is 1, 2, 3 or 4. Preferred $n^1$ is 1 or 2 for increasing the reactivity. Further preferred n is 1.

When both $P^1$ and $P^3$ are group (P-4), at least one of $Sp^1$ and $Sp^3$ is alkylene in which at least one of —CH$_2$— is replaced by —O—, —COO—, —OCO— or —OCOO—. More specifically, both $P^1$ and $P^3$ in no way are alkenyl such as 1-propenyl.

$P^4$, $P^5$ and $P^6$ are independently a group represented by formulas (P-1) to (P-3). Preferred $P^4$, $P^5$ or $P^6$ is group (P-1) and group (P-2). Further preferred group (P-1) is —OCO—CH═CH$_2$ or —OCO—C(CH$_3$)═CH$_2$. A wavy line from group (P-1) to group (P-3) shows a site to form a bonding.

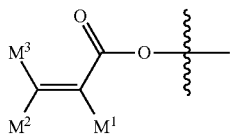
(P-1)

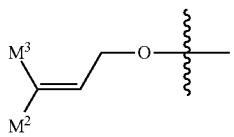
(P-2)

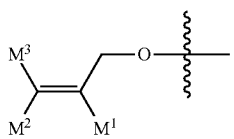
(P-3)

When all of $P^4$, $P^5$ and $P^6$ are group (P-1), $M^1$ (or $M^2$ or $M^3$) of $P^4$, $M^1$ of $P^5$ or $M^1$ of $P^6$ may be identical or different.

$Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$—CH$_2$— may be replaced by —CH═CH— or and in the groups, at least one of hydrogen may be replaced by fluorine or chlorine. Preferred $Sp^1$, $Sp^2$ or $Sp^3$ is a single bond.

Ring G and ring J are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Preferred ring G or ring J is phenyl. Ring I is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Particularly preferred ring I is 1,4-phenylene or 2-fluoro-1,4-phenylene.

$Z^8$ and $Z^9$ are independently a single bond or alkylene having 1 to 10 carbons, and in the alkylene, at least one of —CH$_2$— may be replaced by —O—, —CO—, —COO— or —OCO—, and at least one of —CH$_2$—CH$_2$— may be replaced by —CH═CH—, —C(CH$_3$)═CH—, —CH═C(CH$_3$)— or —C(CH$_3$)═C(CH$_3$)—, and in the groups, at least one of hydrogen may be replaced by fluorine or chlorine. Preferred $Z^8$ or $Z^9$ is a single bond, —CH$_2$CH$_2$—, —CH$_2$O—, —OCH$_2$—, —COO— or —OCO—. Further preferred $Z^8$ or $Z^9$ is a single bond.

Then, h is 0, 1 or 2. Preferred h is 0 or 1. Then, j, k and m are independently 0, 1, 2, 3 or 4, and a sum of j, k and m is 1 or more. Preferred j, k or m is 1 or 2.

Fifth, the preferred component compounds will be described. Preferred compound (1) includes compound (1-1) to compound (1-3) described above. In the compounds, at least one of the first component preferably includes compound (1-1) or compound (1-2). At least two of the first components preferably includes a combination of compound (1-1) and compound (1-2). Further preferred compound (1) includes compound (1-1-1) to compound (1-2-2) described above. At least one of the first component preferably includes compound (1-1-1), compound (1-1-8), compound (1-2-1) or compound (1-2-2). At least two of the first components preferably includes a combination of compound (1-1-1) and compound (1-1-8).

Preferred compound (2) includes compound (2-1) to compound (2-19) described above. In the compounds, at least one of the second component preferably includes compound (2-1), compound (2-3), compound (2-4), compound (2-6), compound (2-8) or compound (2-13). At least two of the second components preferably includes a combination of compound (2-1) and compound (2-6), a combination of compound (2-1) and compound (2-13), a combination of compound (2-3) and compound (2-6), a combination of compound (2-3) and compound (2-13) or a combination of compound (2-4) and compound (2-8).

Preferred compound (3) includes compound (3-1) to compound (3-13) described above. In the compounds, at least one of the third component preferably includes compound (3-1), compound (3-3), compound (3-5), compound (3-6), compound (3-7) or compound (3-8). At least two of the third components preferably includes a combination of compound (3-1) and compound (3-3), a combination of compound (3-1) and compound (3-5) or a combination of compound (3-1) and compound (3-6).

Preferred compound (4) includes compound (4-1) to compound (4-27) described above. In the compounds, at least one of the additive component preferably includes compound (4-1), compound (4-2), compound (4-24), compound (4-25), compound (4-26) or compound (4-27). At least two of the additive components preferably includes a combination of compound (4-1) and compound (4-2), a combination of compound (4-1) and compound (4-18), a combination of compound (4-2) and compound (4-24), a combination of compound (4-2) and compound (4-25), a combination of compound (4-2) and compound (4-26), a combination of compound (4-25) and compound (4-26) or a combination of compound (4-18) and compound (4-24). In group (P-1) to group (P-3), preferred $M^1$, $M^2$ or $M^3$ is hydrogen or methyl. Preferred $Sp^1$, $Sp^2$ or $Sp^3$ is a single bond, —$CH_2CH_2$—, —$CH_2O$—, —$OCH_2$—, —COO—, —OCO—, —CO—CH=CH— or —CH=OH—CO—.

Sixth, the additive that may be added to the composition will be described. Such an additive includes the optically active compound, the antioxidant, the ultraviolet light absorber, the dye, the antifoaming agent, the polymerizable compound, the polymerization initiator, the polymerization inhibitor or the like. The optically active compound is added to the composition for inducing a helical structure in a liquid crystal to give a twist angle. Examples of such a compound include compound (5-1) to compound (5-5). A preferred ratio of the optically active compound is about 5% by weight or less. A further preferred ratio is in the range of about 0.01% by weight to about 2% by weight.

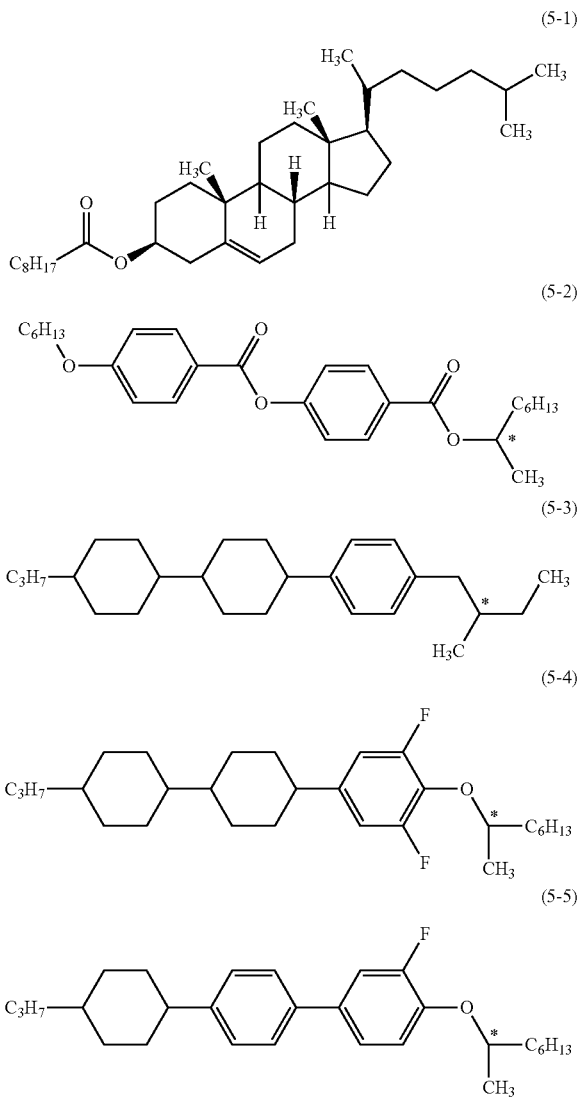

The antioxidant is added to the composition for preventing a decrease in the specific resistance caused by heating in air, or for maintaining a large voltage holding ratio at room temperature and also at the temperature close to the maximum temperature after the device has been used for a long period of time.

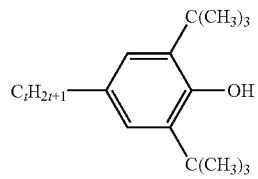

Preferred examples of the antioxidant include compound (6) where t is an integer from 1 to 9 or the like. In compound (6), preferred t is 1, 3, 5, 7 or 9. Further preferred t is 1 or 7. Compound (6) where t is 1 is effective for preventing the decrease in the specific resistance caused by heating in air because the compound (6) has a large volatility. Compound (6) where t is 7 is effective for maintaining the large voltage holding ratio at room temperature and also at the temperature close to the maximum temperature even after the device has been used for a long period of time because the compound (6) has a small volatility. A preferred ratio of the antioxidant is about 50 ppm or more for achieving an effect thereof, and about 600 ppm or less for avoiding a decrease in the maximum temperature or an increase in the minimum temperature. A further preferred ratio is in the range of about 100 ppm to about 300 ppm.

Preferred examples of the ultraviolet light absorber include a benzophenone derivative, a benzoate derivative and a triazole derivative. A light stabilizer such as an amine having steric hindrance is also preferred. A preferred ratio of the absorber or the stabilizer is about 50 ppm or more for achieving an effect thereof, and about 10,000 ppm or less for avoiding the decrease in the maximum temperature or avoiding the increase in the minimum temperature. A further preferred ratio is in the range of about 100 ppm to about 10,000 ppm.

A dichroic dye such as an azo dye or an anthraquinone dye is added to the composition for the purpose of adapting the composition to a device having a guest host (GH) mode. A preferred ratio of the dye is in the range of about 0.01% by weight to about 10% by weight. The antifoaming agent such as dimethyl silicone oil or methyl phenyl silicone oil is added to the composition for preventing foam formation. A preferred ratio of the antifoaming agent is about 1 ppm or more for achieving an effect thereof, and about 1,000 ppm or less for avoiding a poor display. A further preferred ratio is in the range of about 1 ppm to about 500 ppm.

The polymerizable compound is used to be adapted for a polymer sustained alignment (PSA) mode device. Compound (4) is suitable for the purpose. Any other polymerizable compound that is different from compound (4) may be added to the composition together with compound (4). Preferred examples of the polymerizable compounds include acrylate, methacrylate, a vinyl compound, a vinyloxy compound, propenyl ether, an epoxy compound (oxirane and oxetane) and a vinyl ketone compound. Further preferred examples include an acrylate derivative or a methacrylate derivative. A preferred ratio of compound (4) is 10% by weight or more based on the total weight of the polymerizable compound. A further preferred ratio is 50% by weight or more. A particularly preferred ratio is 80% by weight or more. A most preferred ratio is 100% by weight.

The polymerizable compound such as compound (4) is polymerized by irradiation with ultraviolet light. The polymerizable compound may be polymerized in the presence of a suitable initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocur 1173 (registered trademark; BASF), each being a photoinitiator, is suitable for radical polymerization. A preferred ratio of the photopolymerization initiator is in the range of about 0.1% by weight to about 5% by weight based on the total weight of the polymerizable compound. A further preferred ratio is in the range of about 1% by weight to about 3% by weight based thereon.

Upon storing the polymerizable compound such as compound (4), the polymerization inhibitor may be added thereto for preventing polymerization. The polymerizable compound is ordinarily added to the composition without removing the polymerization inhibitor. Examples of the polymerization inhibitor include hydroquinone and a hydroquinone derivative such as methylhydroquinone, 4-tert-butylcatechol, 4-methoxyphenol or phenothiazine.

Seventh, the methods for synthesizing the component compounds will be described. The compounds can be prepared according to known methods. Examples of the synthetic methods are described.

Synthesis of Compound (1-1-1)

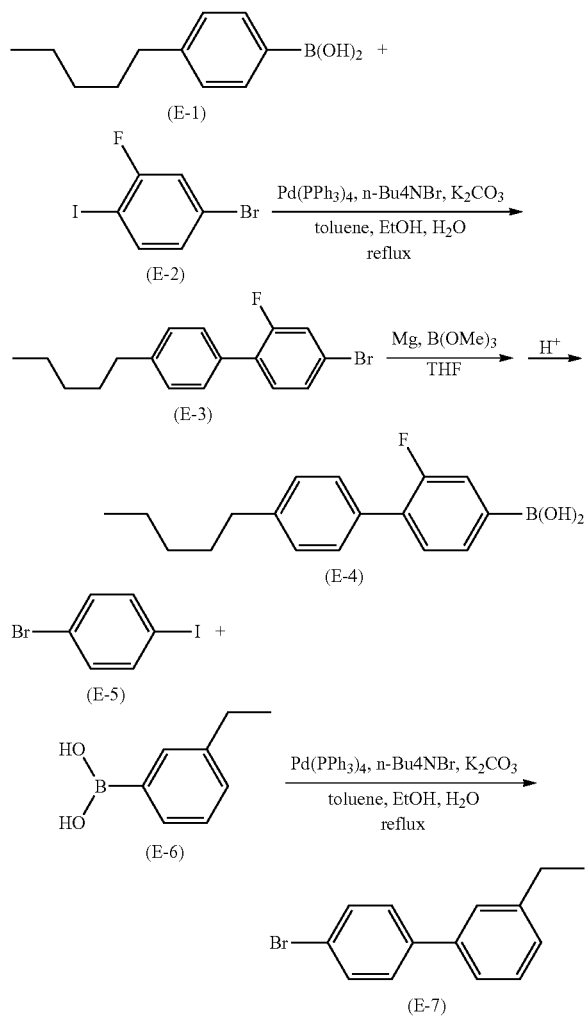

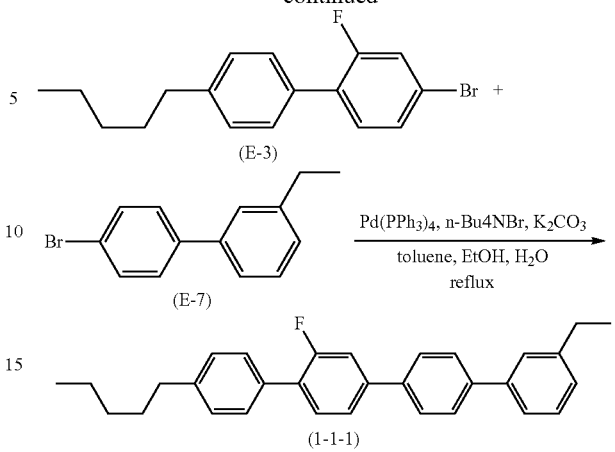

First Step

In a reaction vessel under a nitrogen atmosphere, (4-pentylphenyl)boronic acid (E-1) (26.8 g, 139.58 mmol), 4-bromo-2-fluoro-1-iodobenzene (E-2) (40.0 g, 132.94 mmol), tetrakistriphenyl phosphine palladium (1.54 g, 1.33 mmol), potassium carbonate (27.6 g, 199.41 mmol) and tetrabutylammonium bromide (10.71 g, 33.23 mmol) were put in a mixed solvent of 200 mL of toluene, 50 mL of ethanol and 200 mL of water, and the resulting mixture was refluxed for 8 hours. The resulting react ion mixture was subjected to extraction using toluene. A combined organic layer was washed with water and saturated brine, and dried over magnesium sulfate, and then a solvent was distilled off using an evaporator. The resulting residue was purified by silica gel column chromatography and recrystallized to give 4-bromo-2-fluoro-4'-pentyl-1,1'-biphenyl (E-3) (35.1 g, yield: 78.3%).

Second Step

In a reaction vessel under a nitrogen atmosphere, to a THF (50 mL) suspension of magnesium (2.92 g, 120.20 mmol), a THF (200 mL) solution of compound (E-3) (35.1 g, 109.27 mmol) obtained in the first step was added dropwise at 50° C. or lower. The resulting reaction mixture was stirred at room temperature for 1 hour, and then cooled down to −60° C. or lower, and a THF solution (100 mL) of trimethyl borate (13.6 g, 131.12 mmol) was added dropwise thereto. The resulting reaction mixture was returned to room temperature, and quenched using 3 N hydrochloric acid, and then subjected to extraction using toluene. A combined organic layer was washed with water and saturated brine, and dried over magnesium sulfate, and then a solvent was distilled off using an evaporator. The resulting residue was washed with heptane to give (2-fluoro-4'-pentyl-[1,1'-biphenyl]-4-yl)boronic acid (E-4) (21.4 g, yield: 68.4%).

Third Step

In a reaction vessel under a nitrogen atmosphere, 1-bromo-4-iodobenzene (E-5) (19.6 g, 69.10 mmol), 3-ethylphenylboronic acid (E-6) (11.4 g, 76.01 mmol), tetrakistriphenyl phosphine palladium (2.4 g, 2.07 mmol), potassium carbonate (14.3 g, 103.65 mmol) and tetrabutylammonium bromide (5.57 g, 17.27 mmol) were put in a mixed solvent of 100 mL of toluene, 20 mL of ethanol and 100 mL of water, and the resulting mixture was refluxed for 8 hours. The resulting reaction mixture was subjected to extraction using toluene. A combined organic layer was washed with water and saturated brine, and dried over magnesium sulfate, and then a solvent was distilled off using an evaporator. The resulting residue was purified by silica gel column chromatography to give 4'-bromo-3-ethyl-1,1'-biphenyl (E-7) (15.5 g, yield: 83.5%).

Fourth Step

In a reaction vessel under a nitrogen atmosphere, compound (E-4) (15.9 g, 55.52 mmol) obtained in the second step, compound (E-7) (14.5 g, 55.52 mmol) obtained in the third step, tetrakistriphenyl phosphine palladium (0.64 g, 0.55 mmol), potassium carbonate (11.5 g, 83.28 mmol) and tetrabutylammonium bromide (4.47 g, 13.88 mmol) were put in a mixed solvent of 100 mL of toluene, 20 mL of ethanol and 100 mL of water, and the resulting mixture was refluxed for 8 hours. The resulting reaction mixture was subjected to extraction using toluene. A combined organic layer was washed with water and saturated brine, and dried over magnesium sulfate, and then a solvent was distilled off using an evaporator. The resulting residue was purified by silica gel column chromatography and recrystallized to give compound (1-1-1) (17.4 g, yield: 74.2%).

$^1$H-NMR (CDCl$_3$) δ: 7.71-7.67 (m, 4H), 7.55-7.36 (m, 8H), 7.30-7.26 (m, 2H), 7.24-7.20 (m, 1H), 2.72 (q, 2H), 2.66 (t, 2H), 1.67 (tt, 2H), 1.40-1.34 (m, 4H), 1.31 (t, 3H), 0.92 (t, 3H).

A liquid crystal composition was prepared from 10% by weight of compound (1-1-1) and 90% by weight of a base liquid crystal. Values of characteristics of the resulting liquid crystal composition were measured, and values of characteristics of compound (1-1-1) were calculated by extrapolate the measured value. The thus obtained results were as described below.

Maximum temperature (NI)=132.7° C.; dielectric anisotropy (Δ∈)=5.1; optical anisotropy (Δn)=0.287; viscosity (q)=92.7 mPa·s.

Compound (2-1) is prepared by a method described in JP 2000-053602 A. Compound (3-1) and compound (3-5) are prepared by a method described in JP S59-176221 A. Compound (4) is prepared with reference to JP 2012-001526 A and WO 2010-131600 A. Compound (4-18) is prepared by a method described in JP H7-101900 A. The antioxidant is commercially available. A compound where t in formula (6) is 1 can be obtained from Sigma-Aldrich Corporation. A compound where t in compound (6) is 7 or the like can be prepared according to a method described in U.S. Pat. No. 3,660,505 B.

Any compounds whose synthetic methods are not described can be prepared according to methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition of the invention mainly has a minimum temperature of about −10° C. or lower, a maximum temperature of about 70° C. or higher, and an optical anisotropy in the range of about 0.07 to about 0.20. A device including the composition has the large voltage holding ratio. The composition is suitable for use in the AM device. The composition is particularly suitable for use in a transmissive AM device. The composition having an optical anisotropy in the range of about 0.08 to about 0.25 may be prepared by controlling the ratio of the component compounds or by mixing any other liquid crystal compound, and further the composition having an optical anisotropy in the range of about 0.10 to about 0.30 may be prepared. The composition can be used as the composition having the nematic phase, and as the optically active composition by adding the optically active compound.

The composition can be used for the AM device. The composition can also be used for a PM device. The composition can also be used for an AM device and a PM device each having a mode such as the PC mode, the TN mode, the STN mode, the ECB mode, the OCB mode, the IPS mode, the FFS mode, the VA mode and the FPA mode. Use for the AM device having the TN mode, the OCB mode, the IPS mode or the FFS mode is particularly preferred. In the AM device having the IPS mode or the FFS mode, alignment of liquid crystal molecules when no voltage is applied may be parallel or vertical to a glass substrate. The device may be of a reflective type, a transmissive type or a transflective type. Use for the transmissive device is preferred. Use for an amorphous silicon-TFT device or a polycrystal silicon-TFT device is allowed. The composition can also be used for a nematic curvilinear aligned phase (NCAP) device prepared by microencapsulating the composition, or for a polymer dispersed (PD) device in which a three-dimensional network-polymer is formed in the composition.

One example of the method for manufacturing the device having the polymer sustained alignment mode is as described below. A device having two substrates referred to as an array substrate and a color filter substrate is prepared. At least one of the substrates has an electrode layer. The liquid crystal composition is prepared by mixing the liquid crystal compounds. The polymerizable compound is added to the composition. The additive may be further added when necessary. The composition is injected into the device. The device is irradiated with light in a state in which voltage is applied. Irradiation with ultraviolet light is preferred. The polymerizable compound is polymerized by irradiation with light. The composition containing the polymer is formed by the polymerization. The liquid crystal display device having the polymer sustained alignment mode is manufactured in such a procedure.

In the procedure, when voltage is applied, the liquid crystal molecules are aligned due to an effect of an electric field. Molecules of the polymerizable compound are also aligned according to the alignment. The polymerizable compound is polymerized by irradiation with ultraviolet light in the above state, and therefore the polymer in which the alignment is maintained is formed. The response time of the device is shortened due to an effect of the polymer. The image persistence is caused due to poor operation in the liquid crystal molecules, and therefore is to be simultaneously improved by the effect of the polymer. In addition, the polymerizable compound in the composition is previously polymerized, and the composition may be arranged between the substrates in the liquid crystal display device.

EXAMPLES

The invention will be described in greater detail by way of Examples. However, the invention is not limited by the Examples. The invention includes a mixture of a composition in Example 2 and a composition in Example 3. The invention also includes a mixture in which at least two compositions in Examples are mixed. The thus prepared compound was identified by methods such as an NMR analysis. Characteristics of the compound and the composition were measured by methods described below.

NMR analysis: For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MH$_Z$ and 16 times of accumulation. Tetramethylsilane (TMS) was used as an internal standard. In $^{19}$F-NMR measurement, CFCl$_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: GC-14B Gas Chromatograph made by Shimadzu Corporation was used for measurement. A carrier gas was helium (2 mL/per minute). A sample injector and a detector (FID) were set to 280° C. and 300° C., respectively. A capillary column DB-1 (length 30 m, bore 0.32 mm, film thickness 0.25 µm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane or the like may also be used. The following capillary columns may also be used for separating component compounds: HP-1 (length 30 m, bore 0.32 mm, film thickness 0.25 µm) made by Agilent Technologies, Inc., Rtx-1 (length 30 m, bore 0.32 mm, film thickness 0.25 µm) made by Restek Corporation and BP-1 (length 30 m, bore 0.32 mm, film thickness 0.25 µm) made by SGE International Pty. Ltd. A capillary column CBP1-M50-025 (length 50 m, bore 0.25 mm, film thickness 0.25 µm) made by Shimadzu Corporation may also be used for the purpose of avoiding an overlap of peaks of the compounds.

A ratio of liquid crystal compounds contained in the composition may be calculated by the method as described below. The mixture of liquid crystal compounds is detected by gas chromatograph (FID). An area ratio of each peak in the gas chromatogram corresponds to the ratio (weight ratio) of the liquid crystal compound. When the capillary columns described above were used, a correction coefficient of each of the liquid crystal compounds may be regarded as 1 (one). Accordingly, the ratio (% by weight) of the liquid crystal compound is calculated from the area ratio of each peak.

Sample for measurement: When characteristics of a composition was measured, the composition was used as a sample as was. Upon measuring characteristics of a compound, a sample for measurement was prepared by mixing the compound (15% by weight) with a base liquid crystal (85% by weight). Values of characteristics of the compound were calculated, according to an extrapolation method, using values obtained by measurement. (Extrapolated value)={(measured value of a sample for measurement)−0.85×(measured value of a base liquid crystal)}/0.15. When a smectic phase (or crystals) precipitates at the ratio thereof at 25° C., a ratio of the compound to the base liquid crystal was changed step by step in the order of (10% by weight:90% by weight), (5% by weight:95% by weight) and (1% by weight: 99% by weight). Values of maximum temperature, optical anisotropy, viscosity and dielectric anisotropy with regard to the compound were determined according to the extrapolation method.

A base liquid crystal described below was used. A ratio of the component compound was expressed in terms of weight percent (% by weight).

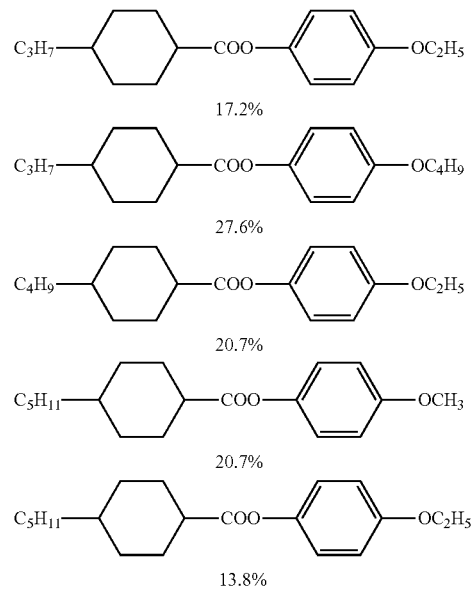

Measuring method: Measurement of characteristics was carried out by the methods described below. Most of the measuring methods are applied as described in the Standard of the Japan Electronics and Information Technology Industries Association (hereinafter abbreviated as JEITA) (JEITA EIAJ ED-25215) discussed and established by JEITA, or modified thereon. No thin film transistor (TFT) was attached to a TN device used for measurement.

(1) Maximum temperature of nematic phase (NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. A maximum temperature of the nematic phase may be occasionally abbreviated as "maximum temperature."

(2) Minimum temperature of nematic phase (T$_c$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., T$_c$ of the sample was expressed as T$_c$<−20° C. A minimum temperature of the nematic phase may be occasionally abbreviated as "minimum temperature."

(3) Viscosity (bulk viscosity; n; measured at 20° C.; mPa·s): A cone-plate (E type) rotational viscometer made by Tokyo Keiki, Inc. was used for measurement.

(4) Viscosity (rotational viscosity; yl; measured at 25° C.; mPa·s): Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was applied repeatedly under the conditions of only one rectangular wave (rectangular pulse; 0.2 second) and no voltage application (2 seconds). A peak current and a peak time of a transient current generated by the applied voltage were measured. A value of rotational viscosity was obtained from the measured values and a calculation equation (8) described on page 40 of the paper presented by M. Imai et al. Dielectric anisotropy required for the calculation was measured according to section (6) described below.

(5) Optical anisotropy (refractive index anisotropy; $\Delta n$; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy was calculated from an equation: $\Delta n = n\| - n\perp$.

(6) Dielectric anisotropy ($\Delta \epsilon$; measured at 25° C.): A value of dielectric anisotropy was calculated from an equation: $\Delta \epsilon = \epsilon\| - \epsilon\perp$. A dielectric constant ($\epsilon\|$ and $\epsilon\perp$) was measured as described below.

(1) Measurement of dielectric constant ($\epsilon\|$): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (E D in a major axis direction of the liquid crystal molecules was measured.

(2) Measurement of dielectric constant ($\epsilon\perp$): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant ($\epsilon\perp$) in a minor axis direction of the liquid crystal molecules was measured.

(7) Threshold voltage (Vth; measured at 25° C.; V): An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(8) Voltage holding ratio (VHR-1a; measured at 25° C.; %): A TN device used for measurement had a polyimide alignment film, and a distance (cell gap) between two glass substrates was 5 micrometers. A sample was put in the device, and the device was sealed with an ultraviolet-curable adhesive. A pulse voltage (60 microseconds at 5 V) was applied to the TN device and the device was charged. A decaying voltage was measured for 166.7 milliseconds with a high-speed voltmeter, and area A between a voltage curve and a horizontal axis in a unit cycle was determined. Area B is an area without decay. A voltage holding ratio is expressed in terms of a percentage of area A to area B.

(9) Voltage holding ratio (VHR-2a; measured at 60° C.; %): A voltage holding ratio was measured according to procedures identical with the procedures described above except that measurement was carried out at 60° C. in place of 25° C. The thus obtained value was expressed in terms of VHR-2a. In a composition containing a polymerizable compound, a TN device was irradiated with ultraviolet light of 25 mW/cm$^2$ for 400 seconds while applying a voltage of 15V to the TN device, and the polymerizable compound in the composition was polymerized. An EXECURE 4000-D type Mercury-Xenon lamp made from HOYA CANDEO OPTRONICS CORPORATION was used for irradiation of ultraviolet light.

(10) Voltage holding ratio (VHR-3a; measured at 60° C.; %): Stability to ultraviolet light was evaluated by measuring a voltage holding ratio after a device was irradiated with ultraviolet light. A TN device used for measurement had a polyimide alignment film and a cell gap was 5 micrometers. A sample was injected into the device, and then the device was irradiated with light for 167 minutes. A light source was black light (peak wavelength of 369 nm), and a distance between the device and the light source was 5 millimeters. In measurement of VHR-3a, a decaying voltage was measured for 166.7 milliseconds. A composition containing a polymerizable compound was polymerized on condition described in (9) item. A composition having large VHR-3a has a large stability to ultraviolet light.

(11) Voltage holding ratio (VHR-4a; measured at 25° C.; %): Stability to heat was evaluated by measuring a voltage holding ratio after a TN device into which a sample was injected was heated in a constant-temperature bath at 80° C. for 500 hours. In measurement of VHR-4a, a decaying voltage was measured for 166.7 milliseconds. A composition having large VHR-4a has a large stability to heat.

(12) Response time (i; measured at 25° C.; ms): An LCD-5100 luminance meter made by Otsuka Electronics Co., Ltd. was used for measurement. A light source was a halogen lamp. A low-pass filter was set at 5 kHz.

(1) A composition containing no polymerizable compound: A sample was put in a normally black mode VA device in which a distance (cell gap) between two glass substrates was 4 micrometers and a rubbing direction was anti-parallel. The device was sealed with an ultraviolet-curable adhesive. A voltage (rectangular waves; 60 Hz, 10 V, 0.5 second) was applied to the device. On the occasion, the device was irradiated with light from a direction perpendicular to the device, and an amount of light transmitted through the device was measured: The maximum amount of light corresponds to 100% transmittance and the minimum amount of light corresponds to 0% transmittance. A response time was expressed in terms of time required for a change from 90% transmittance to 10% transmittance (fall time; millisecond).

(2) A composition containing a polymerizable compound: A sample was put in a normally black mode PVA device in which a distance (cell gap) between two glass substrates was 3.2 micrometers and a rubbing direction was anti-parallel. The device was sealed with an ultraviolet-curable adhesive. The device was irradiated with ultraviolet light of 25 mW/cm² for 400 seconds while applying a voltage of 15V to the device. The EXECURE 4000-D type Mercury-Xenon lamp made from HOYA CANDEO OPTRONICS CORPORATION was used for irradiation of ultraviolet light. Rectangular waves (60 Hz, 10 V, 0.5 second) were applied to the device. On the occasion, the device was irradiated with light from a direction perpendicular to the device, and an amount of light transmitted through the device was measured: The maximum amount of light corresponds to 100% transmittance and the minimum amount of light corresponds to 0% transmittance. A response time was expressed in terms of time required for a change from 0% transmittance to 90% transmittance (rise time; millisecond).

(13) Specific resistance (p; measured at 25 C; Ωcm): Into a vessel equipped with electrodes, 1.0 milliliter of a sample was injected. A direct current voltage (10 V) was applied to the vessel, and a direct current after 10 seconds was measured: Specific resistance was calculated from the following equation: (specific resistance)={(voltage)×(electric capacity of the vessel)}/{(direct current)×(dielectric constant of vacuum)}.

The compounds described in Examples were described using symbols according to definitions in Table 3 below. In Table 3, the configuration of 1,4-cyclohexylene is trans. A parenthesized number next to a symbolized compound in Examples corresponds to the number of the compound. A symbol (-) means any other liquid crystal compound. A ratio (percentage) of the liquid crystal compound is expressed in terms of weight percent (% by weight) based on the weight of the liquid crystal composition. Values of the characteristics of the composition were summarized in the last part.

TABLE 3

| Method for Description of Compounds using Symbols R—(A₁)—Z₁—.....—Zₙ—(Aₙ)—R' | |
|---|---|
| 1) Left-terminal Group R— | Symbol |
| $C_nH_{2n+1}$— | n- |
| $C_nH_{2n+1}O$— | nO- |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |
| $CH_2$=CH—COO— | AC— |
| $CH_2$=C($CH_3$)—COO— | MAC— |
| 2) Right-terminal Group —R' | Symbol |
| —$C_nH_{2n+1}$ | -n |
| —O$C_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —$C_mH_{2m}$—CH=CH—$C_nH_{2n+1}$ | -mVn |
| —CH=$CF_2$ | —VFF |
| —OCO—CH=$CH_2$ | —AC |
| —OCO—C($CH_3$)=$CH_2$ | —MAC |

TABLE 3-continued

| Method for Description of Compounds using Symbols R—(A₁)—Z₁—.....—Zₙ—(Aₙ)—R' | |
|---|---|
| 3) Bonding Group —Zₙ— | Symbol |
| —$C_nH_{2n}$— | n |
| —COO— | E |
| —CH=CH— | V |
| —CH=CHO— | VO |
| —OCH=CH— | OV |
| —$CH_2$O— | 1O |
| —O$CH_2$— | O1 |
| 4) Ring Structure —Aₙ— | Symbol |

H

B

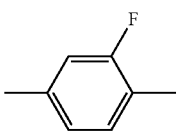
B(F)

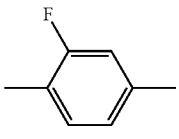
B(2F)

B(F,F)

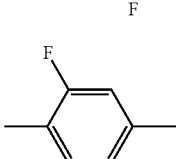
B(2F,5F)

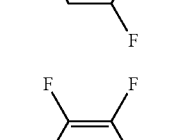
B(2F,3F)

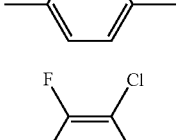
B(2F,3CL)

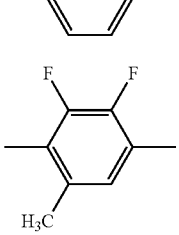
B(2F,3F,6Me)

TABLE 3-continued

Method for Description of Compounds using Symbols
R—(A$_1$)—Z$_1$—.....—Z$_n$—(A$_n$)—R'

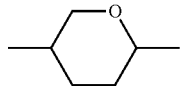 dh

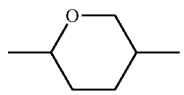 Dh

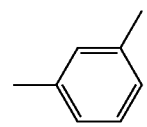 Bm

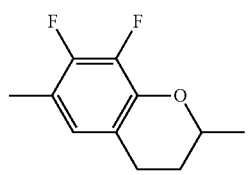 Cro(7F,8F)

5) Examples of Description

Example 1. 3-HH-V1

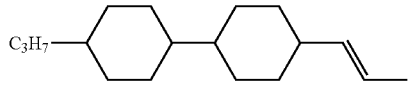

Example 2. MAC-BB-MAC

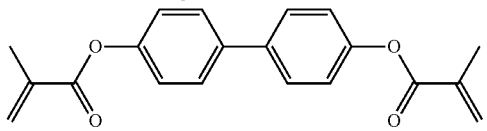

Example 3. 3-DhHB(2F,3F)-O2

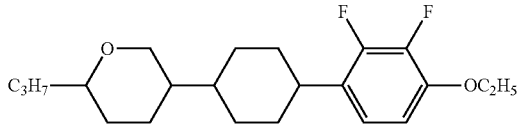

Example 4. 5-BB(2F)BBm-2

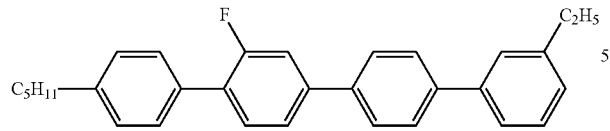

Example 1

| | | |
|---|---|---|
| 5-BB(2F)BBm-2 | (1-1-1) | 0.5% |
| 3-H1OB(2F,3F)-O2 | (2-3) | 4.0% |
| V2-BB(2F,3F)-O1 | (2-4) | 5.0% |
| V2-BB(2F,3F)-O2 | (2-4) | 9.0% |
| 1V2-BB(2F,3F)-O2 | (2-4) | 6.0% |
| V-HHB(2F,3F)-O1 | (2-6) | 3.0% |
| V-HHB(2F,3F)-O2 | (2-6) | 10.0% |
| 3-HH1OB(2F,3F)-O2 | (2-8) | 11.0% |
| 2-BB (2F, 3F) B-3 | (2-9) | 9.0% |
| 3-HH-V | (3-1) | 27.0% |
| 3-HH-V1 | (3-1) | 9.0% |
| 3-HHB-O1 | (3-5) | 3.0% |
| V-HHB-1 | (3-5) | 3.5% |

A composition having negative dielectric anisotropy was prepared, and characteristics thereof were measured.
NI=75.3° C.; T$_c$<−20° C.; Δn=0.112; Δ∈=−3.1; Vth=2.31 V; t=3.9 ms; VHR-2a=93.3%; VHR-3a=48.5%.

Example 2

To the composition in Example 1, compound (4-2-1), compound (4-25-1) and compound (4-26-1) were added at a ratio of 0.01% by weight, a ratio of 0.1% by weight and a ratio of 0.2% by weight, respectively.
MAC-VO-BB-OV-MAC (4-2-1)

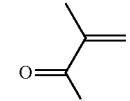

(4-25-1)

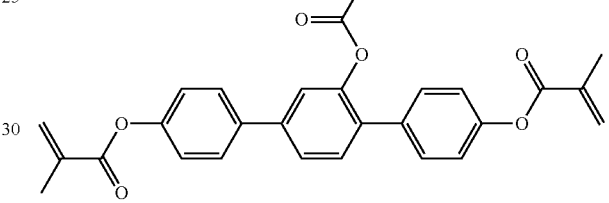

(4-26-1)

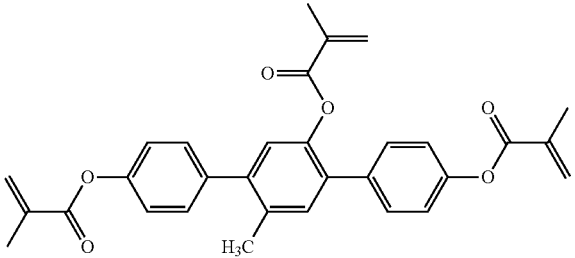

A liquid crystal composition after adding the compounds thereto was injected into the above TN device, and photopolymerization was performed by irradiation with ultraviolet light, and then a voltage holding ratio (VHR-2a and VHR-3a) was measured.
VHR-2a=95.5%; VHR-3a=55.6%.

Comparative Example 1

A composition that contains no compound (1-1-1) was prepared. In the composition in Example 1, twelve compounds excluding compound (1-1-1) were mixed at a same ratio. Characteristics of the composition were measured.
NI=75.3° C.; T$_c$<−20° C.; Δn=0.111; Δ∈=−3.1; Vth=2.30 V; t=4.0 ms; VHR-2a=88.7%; VHR-3a=33.4%.

Comparative Example 2

To the composition in Comparative Example 1, compound (4-2-1), compound (4-25-1) and compound (4-26-1) were added at a ratio of 0.01% by weight, a ratio of 0.1% by weight and a ratio of 0.2% by weight, respectively.

MAC-VO-BB-OV-MAC (4-2-1)

(4-25-1)

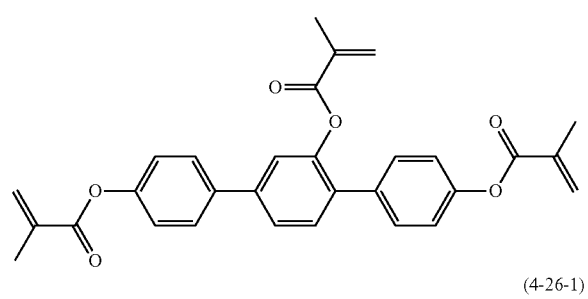

(4-26-1)

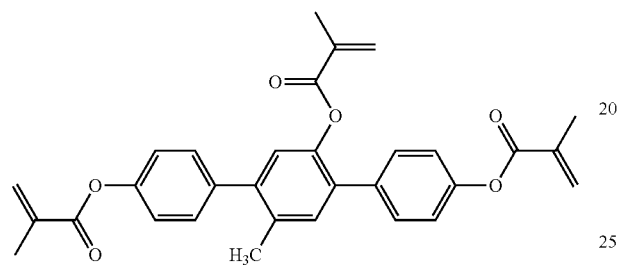

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=91.3%; VHR-3a=37.1%.

A voltage holding ratio (VHR-2a) of the composition in Example 1 was 93.3%, and the voltage holding ratio (VHR-2a) of the composition in Comparative Example 1 was 88.7%. A voltage holding ratio (VHR-3a) of the composition in Example 1 was 48.5%, and the voltage holding ratio (VHR-3a) of the composition in Comparative Example 1 was 33.4%. From the results, a TN device in Example 1 was found to have a larger voltage holding ratio in comparison with a TN device in Comparative Example 1.

A voltage holding ratio (VHR-2a) of the composition in Example 2 was 95.5%, and the voltage holding ratio (VHR-2a) of the composition in Comparative Example 2 was 91.3%. A voltage holding ratio (VHR-3a) of the composition in Example 2 was 55.6%, and the voltage holding ratio (VHR-3a) of the composition in Comparative Example 2 was 37.1%. Accordingly, the liquid crystal composition according to the invention is concluded to have superb characteristics in view of a liquid crystal display device having a polymer sustained alignment mode.

Example 3

| 5-B(F)BB(2F)Bm-2 | (1-1-3) | 1.0% |
| 3-H1OB(2F,3F)-O2 | (2-3) | 8.0% |
| V2-BB(2F,3F)-O1 | (2-4) | 5.0% |
| V2-BB(2F,3F)-O2 | (2-4) | 9.0% |
| 1V2-BB(2F,3F)-O4 | (2-4) | 6.0% |
| V-HHB(2F,3F)-O2 | (2-6) | 10.0% |
| V-HHB(2F,3F)-O4 | (2-6) | 3.0% |
| 1V2-HHB(2F,3F)-O2 | (2-6) | 4.0% |
| 3-HH1OB(2F,3F)-O2 | (2-8) | 11.0% |
| 3-HH-V | (3-1) | 26.0% |
| 1-HH-2V1 | (3-1) | 5.0% |

-continued

| 5-HB-O2 | (3-2) | 3.0% |
| 3-HHB-O1 | (3-5) | 5.0% |
| V-HHB-1 | (3-5) | 4.0% |

A composition having negative dielectric anisotropy was prepared, and characteristics thereof were measured.

NI=74.2° C.; $T_c$<−20° C.; $\Delta n$=0.101; $\Delta\epsilon$=−3.4; Vth=2.19 V.

To the composition, compound (4-25-2) as the additive was added at a ratio of 0.4% by weight.

(4-25-2)

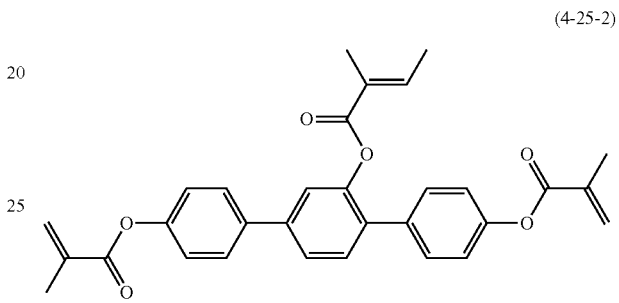

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=95.9%; VHR-3a=55.7%.

Example 4

| 5-B (2F) B (2F) B (2F) Bm-3 | (1-1-7) | 1.2% |
| 5-HBB(2F)B(2F)Bm-2 | (1-2-2) | 0.3% |
| 3-BB(2F,3F)-O2 | (2-4) | 9.0% |
| 2O-BB(2F,3F)-O2 | (2-4) | 3.0% |
| 2-HH1OB(2F,3F)-O2 | (2-8) | 10.0% |
| 3-HH1OB(2F,3F)-O2 | (2-8) | 20.0% |
| 2-HH-3 | (3-1) | 19.0% |
| 3-HH-4 | (3-1) | 4.0% |
| 3-HH-V | (3-1) | 8.0% |
| V2-BB-1 | (3-3) | 3.0% |
| 1-BB-3 | (3-3) | 7.5% |
| V-HHB-3 | (3-5) | 5.0% |
| 3-HBB-2 | (3-6) | 4.0% |
| 5-B(F)BB-2 | (3-7) | 3.0% |
| 5-HBBH-3 | (3-11) | 3.0% |

A composition having negative dielectric anisotropy was prepared, and characteristics thereof were measured.

NI=81.1° C.; $T_c$<−20° C.; $\Delta n$=0.107; $\Delta\epsilon$=−2.6; Vth=2.41 V.

To the composition, compound (4-2-1) and compound (4-25-1) were added at a ratio of 0.01% by weight and a ratio of 0.2% by weight, respectively.

MAC-VO-BB-OV-MAC (4-2-1)

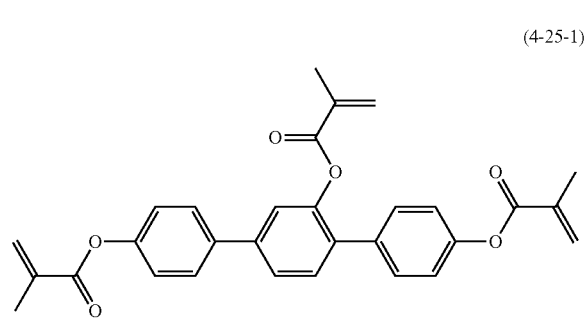 [SMILES: C=C(C)C(=O)Oc1ccc(-c2ccc(-c3ccc(OC(=O)C(=C)C)cc3)c(OC(=O)C(=C)C)c2)cc1]
(4-25-1)

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=96.1%; VHR-3a=58.2%.

Example 5

| | | |
|---|---|---|
| 5-B(F)BB(2F)Bm-2 | (1-1-3) | 0.3% |
| V2-BB(F)BBm-3 | (1-1-8) | 0.3% |
| 3-BB(2F,3F)-O2 | (2-4) | 10.0% |
| 5-BB(2F,3F)-O4 | (2-4) | 3.0% |
| 2-HH1OB(2F,3F)-O2 | (2-8) | 10.0% |
| 3-HH1OB(2F,3F)-O2 | (2-8) | 21.4% |
| 2-HH-3 | (3-1) | 21.0% |
| 3-HH-V | (3-1) | 8.0% |
| 1-BB-3 | (3-3) | 8.0% |
| 1V2-BB-1 | (3-3) | 3.0% |
| V2-HHB-1 | (3-5) | 5.0% |
| 3-HBB-2 | (3-6) | 4.0% |
| 5-B(F)BB-3 | (3-7) | 3.0% |
| 1O1-HBBH-4 | (—) | 3.0% |

A composition having negative dielectric anisotropy was prepared, and characteristics thereof were measured.

NI=78.3° C.; $T_c$<−20° C.; Δn=0.107; Δ∈=−2.5; Vth=2.44 V;

To the composition, compound (4-25-1) and compound (4-25-2) were added at a ratio of 0.15% by weight and a ratio of 0.05% by weight, respectively.

MAC-VO-BB-OV-MAC (4-2-1)

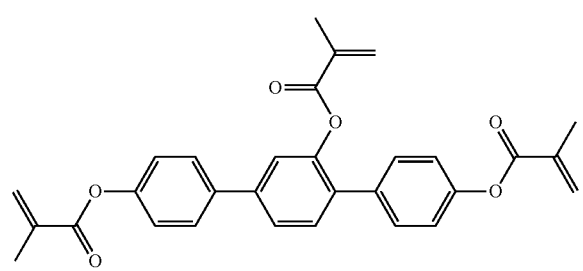
(4-25-1)

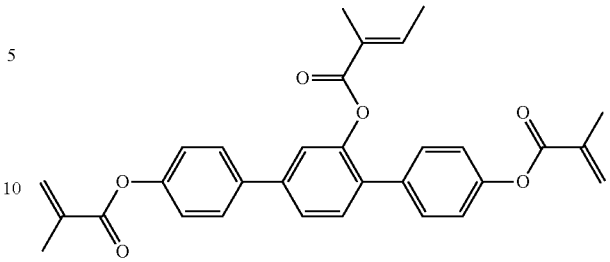
(4-25-2)

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=96.3%; VHR-3a=56.8%.

Example 6

| | | |
|---|---|---|
| 5-BB(2F)BBm-2 | (1-1-1) | 0.3% |
| 5-HBB(2F)BBm-2 | (1-2-1) | 0.3% |
| V2-BB(2F,3F)-O2 | (2-4) | 12.0% |
| 1V2-BB(2F,3F)-O2 | (2-4) | 6.0% |
| 1V2-BB(2F,3F)-O4 | (2-4) | 3.0% |
| V-HHB(2F,3F)-O1 | (2-6) | 6.0% |
| V-HHB(2F,3F)-O2 | (2-6) | 12.0% |
| V-HHB(2F,3F)-O4 | (2-6) | 5.0% |
| 3-HDhB(2F,3F)-O2 | (2-11) | 5.0% |
| 3-dhBB(2F,3F)-O2 | (2-14) | 4.4% |
| 3-HH-V | (3-1) | 29.0% |
| 1-BB-3 | (3-3) | 6.0% |
| V-HHB-1 | (3-5) | 5.0% |
| 1-BB(F)B-2V | (3-8) | 3.0% |
| 3-HHEBH-4 | (3-9) | 3.0% |

A composition having negative dielectric anisotropy was prepared, and characteristics thereof were measured.

NI=78.2° C.; $T_c$<−20° C.; Δn=0.114; Δ∈=−2.9; Vth=2.33 V.

To the composition, compound (4-2-2) described below was added at a ratio of 0.3% by weight.

MAC-BB-MAC (4-2-2)

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=97.7%; VHR-3a=65.4%.

Example 7

| | | |
|---|---|---|
| 3-BB(F)BBm-2 | (1-1-8) | 0.3% |
| V2-BB(2F,3F)-O2 | (2-4) | 12.0% |
| 1V2-BB(2F,3F)-O2 | (2-4) | 6.0% |
| 1V2-BB(2F,3F)-O4 | (2-4) | 3.0% |
| V-HHB(2F,3F)-O1 | (2-6) | 6.0% |
| V-HHB(2F,3F)-O2 | (2-6) | 7.0% |
| V-HHB(2F,3F)-O4 | (2-6) | 5.0% |
| 1V2-HHB(2F,3F)-O4 | (2-6) | 5.0% |
| 3-HDhB(2F,3F)-O2 | (2-11) | 5.0% |
| 3-dhBB(2F,3F)-O2 | (2-14) | 5.0% |
| 3-HH-V | (3-1) | 28.7% |
| V2-HB-1 | (3-2) | 6.0% |

| | | |
|---|---|---|
| V-HHB-1 | (3-5) | 5.0% |
| 2-BB(F)B-5 | (3-8) | 3.0% |
| 5-HBB(F)B-3 | (3-13) | 3.0% |

A composition having negative dielectric anisotropy was prepared, and characteristics thereof were measured.

NI=78.9° C.; $T_c$<−20° C.; Δn=0.113; Δ∈=−2.9; Vth=2.36 V.

To the composition, compound (4-1-1) described below was added at a ratio of 0.3% by weight.

MAC-B(2F)B-MAC (4-1-1)

A liquid crystal composition after adding the compounds thereto was injected into the above TN device, and photo-polymerization was performed by irradiation with ultraviolet light, and then a voltage holding ratio (VHR-2a and VHR-3a) was measured.

VHR-2a=97.6%; VHR-3a=63.7%.

Example 8

| | | |
|---|---|---|
| 3-BB(2F)BBm-2 | (1-1-1) | 0.3% |
| 3-HB(2F,3F)-O2 | (2-1) | 3.0% |
| V2-BB(2F,3F)-O2 | (2-4) | 11.7% |
| 1V2-BB(2F,3F)-O2 | (2-4) | 6.0% |
| V2-HHB(2F,3F)-O2 | (2-6) | 5.0% |
| 3-HDhB(2F,3F)-O2 | (2-11) | 5.0% |
| 3-HBB(2F,3F)-O2 | (2-13) | 3.0% |
| V-HBB(2F,3F)-O2 | (2-13) | 6.0% |
| V2-HBB(2F,3F)-O2 | (2-13) | 6.0% |
| 3-dhBB(2F,3F)-O2 | (2-14) | 5.0% |
| 5-HH-O1 | (3-1) | 4.0% |
| 3-HH-V | (3-1) | 25.0% |
| 3-HH-VFF | (3-1) | 3.0% |
| 1-BB-3 | (3-3) | 6.0% |
| 3-HHEH-3 | (3-4) | 3.0% |
| V-HHB-1 | (3-5) | 5.0% |
| V2-HHB-1 | (3-5) | 3.0% |

A composition having negative dielectric anisotropy was prepared, and characteristics thereof were measured.

NI=74.2° C.; $T_c$<−20° C.; Δn=0.114; Δ∈=−2.6; Vth=2.37 V.

To the composition, compound (4-25-2) and compound (4-26-1) described below were added at a ratio of 0.15% by weight and at a ratio of 0.15% by weight, respectively.

(4-25-2)

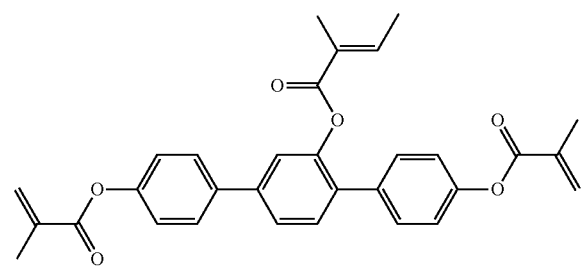

(4-26-1)

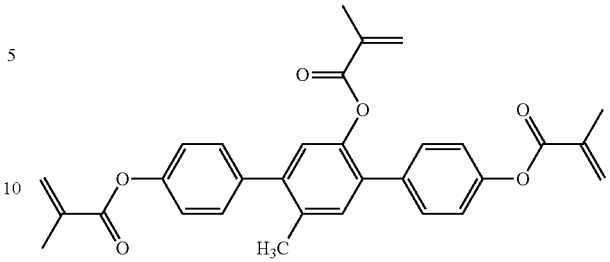

A liquid crystal composition after adding the compounds thereto was injected into the above TN device, and photo-polymerization was performed by irradiation with ultraviolet light, and then a voltage holding ratio (VHR-2a and VHR-3a) was measured.

VHR-2a=97.4%; VHR-3a=59.4%.

Example 9

| | | |
|---|---|---|
| 3-BBB(2F,5F)Bm-2 | (1-1-9) | 0.4% |
| V2-BB(2F,3F)-O2 | (2-4) | 10.0% |
| 1V2-BB(2F,3F)-O2 | (2-4) | 4.0% |
| 1V2-BB(2F,3F)-O4 | (2-4) | 4.0% |
| V-HHB(2F,3F)-O1 | (2-6) | 6.0% |
| V-HHB(2F,3F)-O2 | (2-6) | 10.0% |
| V-HHB(2F,3F)-O4 | (2-6) | 5.0% |
| 3-DhH1OB(2F,3F)-O2 | (2-12) | 3.0% |
| 3-HHB(2F,3CL)-O2 | (2-16) | 3.0% |
| 5-HBB(2F,3CL)-O2 | (2-17) | 3.0% |
| 3-H1OCro(7F,8F)-5 | (2-18) | 3.0% |
| 3-HH1OCro(7F,8F)-5 | (2-19) | 3.0% |
| 3-HH-V | (3-1) | 29.0% |
| 1-BB-3 | (3-3) | 6.0% |
| V-HHB-1 | (3-5) | 7.0% |
| 3-HBB-2 | (3-6) | 3.6% |

A composition having negative dielectric anisotropy was prepared, and characteristics thereof were measured.

NI=75.4° C.; $T_c$<−20° C.; Δn=0.105; Δ∈=−3.0; Vth=2.23 V.

To the composition, compound (4-18-1) described below was added at a ratio of 0.3% by weight.

AC-VO-BB(F)B-OV-AC (4-18-1)

A liquid crystal composition after adding the compounds thereto was injected into the above TN device, and photo-polymerization was performed by irradiation with ultraviolet light, and then a voltage holding ratio (VHR-2a and VHR-3a) was measured.

VHR-2a=96.9%; VHR-3a=58.7%.

Example 10

| | | |
|---|---|---|
| 5-BB(2F,5F)BBm-2 | (1-1-4) | 0.5% |
| 5-BB (2F, 5F) B (2F) Bm-2 | (1-1-5) | 0.5% |
| V2-HB(2F,3F)-O2 | (2-1) | 5.0% |
| 3-H2B(2F,3F)-O2 | (2-2) | 9.0% |
| V-HHB(2F,3F)-O2 | (2-6) | 12.0% |
| 2-HH1OB(2F,3F)-O2 | (2-8) | 7.0% |
| 3-HH1OB(2F,3F)-O2 | (2-8) | 12.0% |
| 3-HDhB(2F,3F)-O2 | (2-11) | 3.0% |
| 2-HH-3 | (3-1) | 22.0% |
| 3-HH-V | (3-1) | 8.0% |
| 1-BB-3 | (3-3) | 9.0% |

-continued

| | | |
|---|---|---|
| 3-HHB-1 | (3-5) | 3.0% |
| 3-B(F)BB-2 | (3-7) | 3.0% |
| 3-HB(F)HH-5 | (3-10) | 3.0% |
| 3-HB(F)BH-3 | (3-12) | 3.0% |

A composition having negative dielectric anisotropy was prepared, and characteristics thereof were measured.
NI=79.0° C.; $T_c$<−20° C.; Δn=0.095; Δ∈=−2.8; Vth=2.35 V.
To the composition, compound (4-27-1) was added at a ratio of 0.1% by weight.

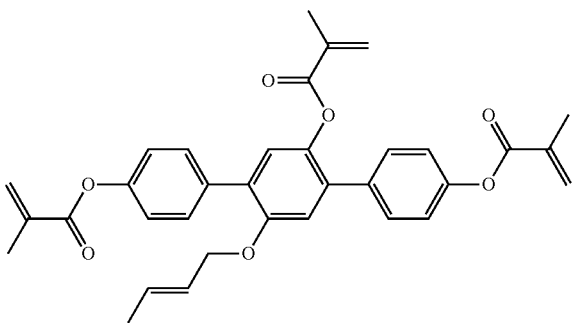

(4-27-1)

To the composition, photopolymerization was performed by irradiation with ultraviolet light, and then a voltage holding ratio (VHR-2a and VHR-3a) was measured.
VHR-2a=96.8%; VHR-3a=57.6%.

Example 11

| | | |
|---|---|---|
| 5-BB(2F)B(2F)Bm-2 | (1-1-2) | 0.5% |
| 1V2-HB(2F,3F)-O2 | (2-1) | 4.5% |
| 5-H2B (2F, 3F) -O2 | (2-2) | 9.0% |
| 5-HHB(2F,3F)-O2 | (2-6) | 3.0% |
| V-HHB(2F,3F)-O2 | (2-6) | 6.0% |
| 2-HH1OB(2F,3F)-O2 | (2-8) | 7.0% |
| 3-HH1OB(2F,3F)-O2 | (2-8) | 12.0% |
| 2-BB (2F, 3F) B-3 | (2-9) | 3.0% |
| 2-HHB(2F,3CL)-O2 | (2-16) | 3.0% |
| 4-HHB(2F,3CL)-O2 | (2-16) | 3.0% |
| 2-HH-3 | (3-1) | 22.0% |
| 3-HH-V | (3-1) | 8.0% |
| 1-BB-3 | (3-3) | 10.0% |
| 3-HHB-1 | (3-5) | 3.0% |
| 3-HB(F)HH-5 | (3-10) | 3.0% |
| 3-HB(F)BH-3 | (3-12) | 3.0% |

A composition having negative dielectric anisotropy was prepared, and characteristics thereof were measured.
NI=81.0° C.; $T_c$<−20° C.; Δn=0.094; Δ∈=−2.8; Vth=2.39 V.
To the composition, compound (4-2-1) and compound (4-18-1) described below were added at a ratio of 0.1% by weight and at a ratio of 0.1% by weight, respectively.
MAC-VO-BB-OV-MAC (4-2-1)
AC-VO-BB(F)B-OV-AC (4-18-1)
A liquid crystal composition after adding the compounds thereto was injected into the above TN device, and photopolymerization was performed by irradiation with ultraviolet light, and then a voltage holding ratio (VHR-2a and VHR-3a) was measured.
VHR-2a=97.0%; VHR-3a=62.9%.

Example 12

| | | |
|---|---|---|
| 3-B (F) B (2F) B (2F) Bm-2 | (1-1-6) | 0.5% |
| 3-HB (2F, 3F)-O4 | (2-1) | 5.0% |
| V-HB(2F,3F)-O2 | (2-1) | 4.0% |
| V2-BB(2F,3F)-O2 | (2-4) | 7.0% |
| 1V2-BB(2F,3F)-O2 | (2-4) | 5.5% |
| 2O-B(2F,3F)B(2F,3F)-O6 | (2-5) | 3.0% |
| V-HHB(2F,3F)-O2 | (2-6) | 10.0% |
| 3-HH2B(2F,3F)-O2 | (2-7) | 3.0% |
| 3-HH1OB(2F,3F)-O2 | (2-8) | 10.0% |
| 2-BB(2F,3F)B-3 | (2-9) | 6.0% |
| 3-HH-V | (3-1) | 27.0% |
| 4-HH-V1 | (3-1) | 6.0% |
| 3-HH-2V1 | (3-1) | 3.0% |
| 3-HBB-2 | (3-6) | 7.0% |
| 5-HBB(F)B-2 | (3-13) | 3.0% |

A composition having negative dielectric anisotropy was prepared, and characteristics thereof were measured.
NI=79.1° C.; $T_c$<−20° C.; Δn=0.112; Δ∈=−3.0; Vth=2.33 V.
To the composition, compound (4-2-1) and compound (4-26-1) described below were added at a ratio of 0.02% by weight and at a ratio of 0.3% by weight, respectively.
MAC-VO-BB-OV-MAC (4-2-1)

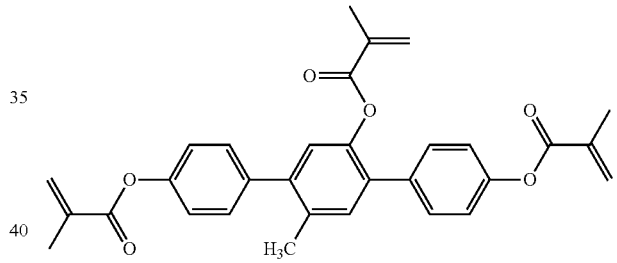

(4-26-1)

A liquid crystal composition after adding the compounds thereto was injected into the above TN device, and photopolymerization was performed by irradiation with ultraviolet light, and then a voltage holding ratio (VHR-2a and VHR-3a) was measured.
VHR-2a=96.7%; VHR-3a=57.4%.

Example 13

| | | |
|---|---|---|
| 5-B (2F) B (2F) B (2F) Bm-3 | (1-1-7) | 0.2% |
| 3-HB(2F,3F)-O2 | (2-1) | 5.0% |
| V-HB(2F,3F)-O4 | (2-1) | 4.0% |
| 5-BB(2F,3F)-O2 | (2-4) | 6.0% |
| V2-BB(2F,3F)-O2 | (2-4) | 7.0% |
| 3-B(2F,3F)B(2F,3F)-O2 | (2-5) | 3.0% |
| V-HHB(2F,3F)-O2 | (2-6) | 10.0% |
| 3-HH1OB(2F,3F)-O2 | (2-8) | 10.0% |
| 2-BB(2F,3F)B-3 | (2-9) | 5.0% |
| 4-HBB(2F,3F)-O2 | (2-13) | 3.0% |
| 3-HBB(2F,3CL)-O2 | (2-17) | 3.0% |
| 3-HH-O1 | (3-1) | 3.0% |
| 3-HH-V | (3-1) | 24.0% |
| 3-HB-O2 | (3-2) | 3.0% |

| | | |
|---|---|---|
| V-HHB-1 | (3-5) | 6.8% |
| 3-BB(F)B-5 | (3-8) | 3.0% |
| 5-HBB(F)B-2 | (3-13) | 4.0% |

A composition having negative dielectric anisotropy was prepared, and characteristics thereof were measured.

NI=77.4° C.; $T_c$<−20° C.; Δn=0.117; Δ∈=−3.1; Vth=2.30 V;

To the composition, compound (4-2-1) and compound (4-23-1) described below were added at a ratio of 0.3% by weight and at a ratio of 0.1% by weight, respectively.

AC-VO-BB-OV-AC (4-2-1)

(4-23-1)

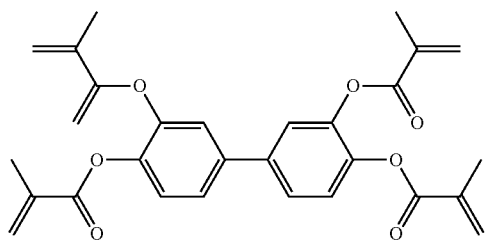

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=96.6%; VHR-3a=54.9%.

Example 14

| | | |
|---|---|---|
| 5-HBB(2F)BBm-2 | (1-2-1) | 0.3% |
| 5-HBB(2F)B(2F)Bm-2 | (1-2-2) | 0.3% |
| 3-BB(2F,3F)-O4 | (2-4) | 5.0% |
| V2-BB(2F,3F)-O2 | (2-4) | 12.0% |
| 1V2-BB(2F,3F)-O1 | (2-4) | 4.0% |
| 3-HHB(2F,3F)-O2 | (2-6) | 5.0% |
| V-HHB(2F,3F)-O1 | (2-6) | 6.0% |
| V-HHB(2F,3F)-O2 | (2-6) | 12.0% |
| 3-DhHB(2F,3F)-O2 | (2-10) | 5.0% |
| 3-HEB(2F,3F)B(2F,3F)-O2 | (2-15) | 5.0% |
| 3-HH-V | (3-1) | 22.4% |
| 4-HH-V | (3-1) | 3.0% |
| 5-HH-V | (3-1) | 6.0% |
| 7-HB-1 | (3-2) | 3.0% |
| V-HHB-1 | (3-5) | 5.0% |
| 3-HBB-2 | (3-6) | 3.0% |
| 2-BB(F)B-3 | (3-8) | 3.0% |

A composition having negative dielectric anisotropy was prepared, and characteristics thereof were measured.

NI=76.9° C.; $T_c$<−20° C.; Δn=0.106; Δ∈=−2.9; Vth=2.25 V.

To the composition, compound (4-24-1) described below was added at a ratio of 0.2% by weight.

(4-24-1)

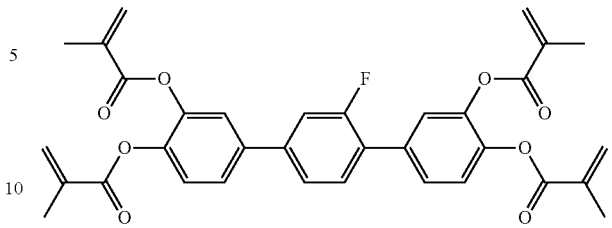

A liquid crystal composition after adding the compounds thereto was injected into the above TN device, and photopolymerization was performed by irradiation with ultraviolet light, and then a voltage holding ratio (VHR-2a and VHR-3a) was measured.

VHR-2a=97.7%; VHR-3a=66.4%.

The compositions in Example 2 to Example 14 were found to have a larger voltage holding ratio (VHR-2a and VHR-3a) in comparison with the composition in Comparative Example 2. Accordingly, the liquid crystal composition according to the invention is concluded to have superb characteristics.

INDUSTRIAL APPLICABILITY

A liquid crystal composition of the invention satisfies at least one of characteristics such as a high maximum temperature, a low minimum temperature, a small viscosity, a suitable optical anisotropy, a large negative dielectric anisotropy, a large specific resistance, a high stability to ultraviolet light, a high stability to heat or the like, or has a suitable balance regarding at least two of the characteristics. A liquid crystal display device including the composition has characteristics such as a short response time, a large voltage holding ratio, a low threshold voltage, a large contrast ratio, a long service life and so forth, and thus can be used for a liquid crystal projector, a liquid crystal television and so forth.

What is claimed is:

1. A liquid crystal composition that has a negative dielectric anisotropy, and contains at least one compound represented by formula (1) as a first component:

(1)

wherein, in formula (1), $R^1$, $R^2$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, in which $R^2$ may be hydrogen; ring A is 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; $Z^1$, $Z^2$, $Z^3$ and $Z^4$ are independently a single bond, —CH$_2$CH$_2$—, —CH$_2$O—, —OCH$_2$—, —COO— or —OCO—; a, b and c are independently 0, 1, 2, 3 or 4; and d is 0, 1 or 2.

2. The liquid crystal composition according to claim 1, containing at least one compound selected from the group of compounds represented by formulas (1-1) to (1-3) as the first component:

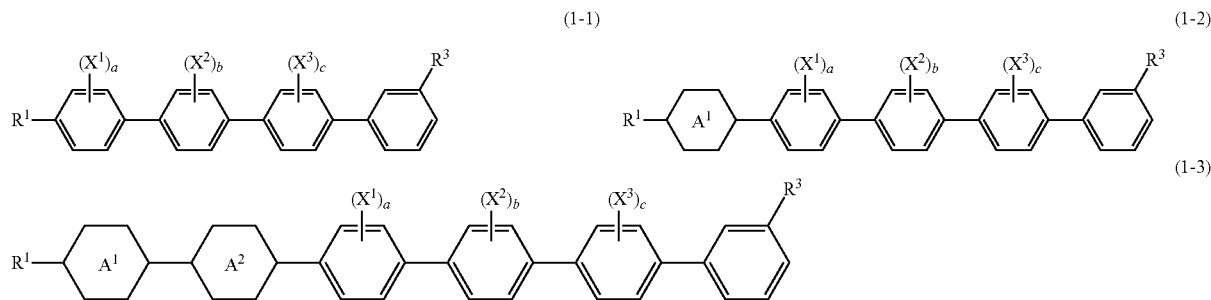

wherein, in formula (1-1) to formula (1-3), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; rings $A^1$ and $A^2$ are independently 1,4-phenylene, 1,4-cyclohexylene, 1,4-cyclohexenylene, 1,3-dioxane-2,5-diyl, tetrahydropyran-2,5-diyl, or 1,4-phenylene in which at least one of hydrogen is replaced by fluorine, chlorine or methyl; $X^1$, $X^2$ and $X^3$ are independently fluorine, chlorine, or alkyl having 1 to 12 carbons in which at least one of hydrogen may be replaced by fluorine; and a, b and c are independently 0, 1, 2, 3 or 4.

3. The liquid crystal composition according to claim 1, containing at least one compound selected from the group of compounds represented by formulas (1-1-1) to (1-1-9), formula (1-2-1) and formula (1-2-2) as the first component:

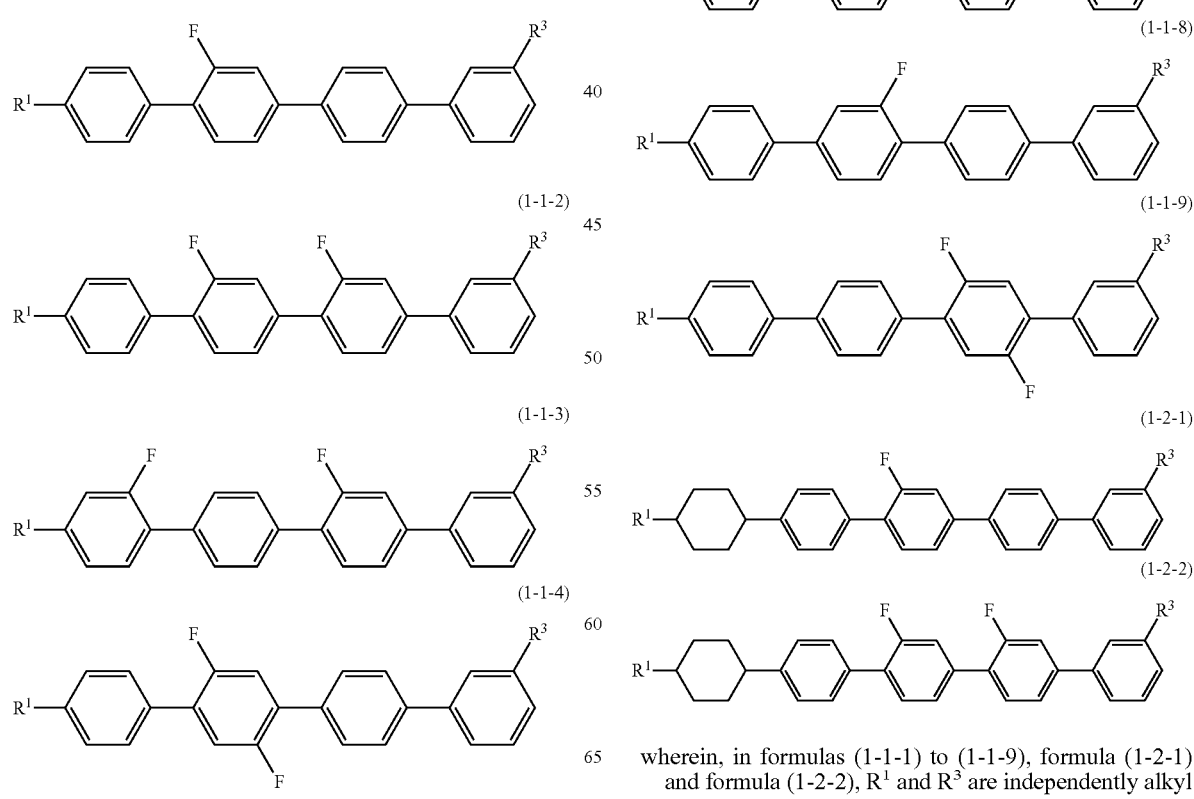

wherein, in formulas (1-1-1) to (1-1-9), formula (1-2-1) and formula (1-2-2), $R^1$ and $R^3$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

4. The liquid crystal composition according to claim 1, wherein a ratio of the first component is in the range of 0.03% by weight to 10% by weight based on the weight of the liquid crystal composition.

5. The liquid crystal composition according to claim 1, containing at least one compound represented by formula (2) as a second component:

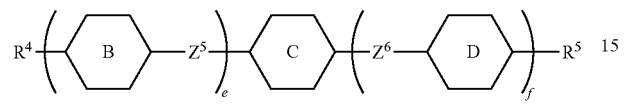
(2)

wherein, in formula (2), $R^4$ and $R^5$ are independently alkyl having 1 to 12 carbons, alkoxy having 1 to 12 carbons, alkenyl having 2 to 12 carbons or alkenyloxy having 2 to 12 carbons; ring B and ring D are independently 1,4-cyclohexylene, 1,4-cyclohexenylene, 1,4-phenylene, 1,4-phenylene in which at least one of hydrogen is replaced by fluorine or chlorine, or tetrahydropyran-2,5-diyl; ring C is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^5$ and $Z^6$ are independently a single bond, —CH$_2$CH$_2$—, —CH$_2$O—, —OCH$_2$—, —COO— or —OCO—; and e is 1, 2 or 3, f is 0 or 1 and a sum of e and f is 3 or less.

6. The liquid crystal composition according to claim 5, containing at least one compound selected from the group of compounds represented by formulas (2-1) to (2-19) as the second component:

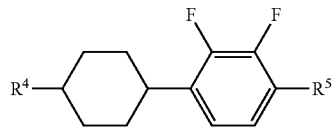
(2-1)

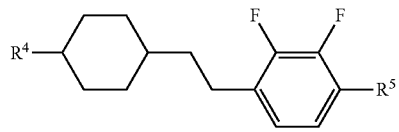
(2-2)

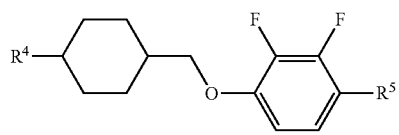
(2-3)

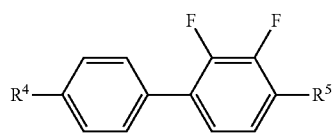
(2-4)

(2-5)

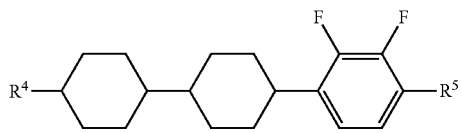
(2-6)

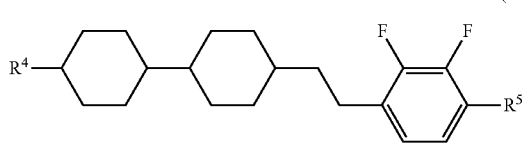
(2-7)

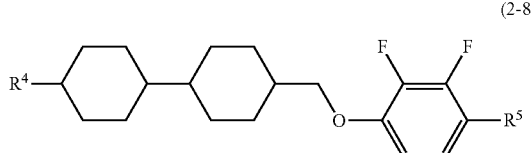
(2-8)

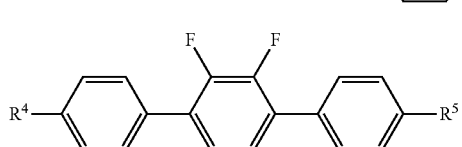
(2-9)

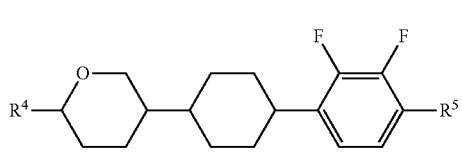
(2-10)

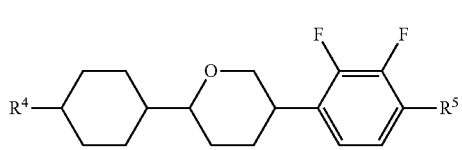
(2-11)

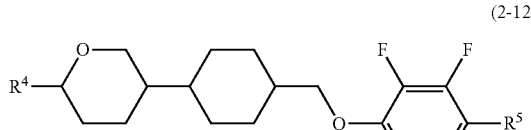
(2-12)

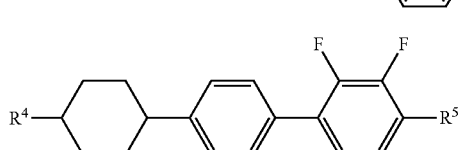
(2-13)

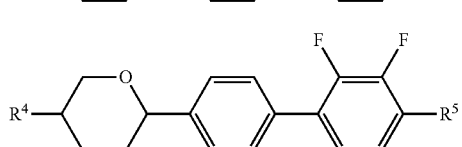
(2-14)

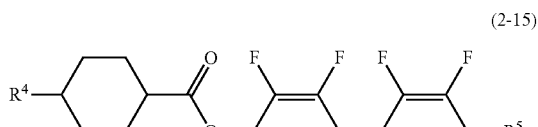
(2-15)

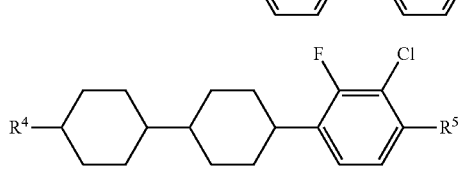
(2-16)

53

-continued

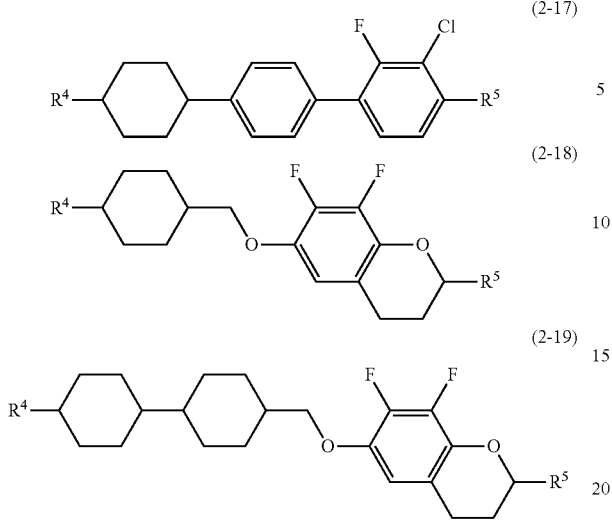

(2-17)

(2-18)

(2-19)

wherein, in formula (2-1) to formula (2-19), $R^4$ and $R^5$ are independently alkyl having 1 to 12 carbons, alkoxy having 1 to 12 carbons, alkenyl having 2 to 12 carbons or alkenyloxy having 2 to 12 carbons.

7. The liquid crystal composition according to claim 5, wherein a ratio of the second component is in the range of 10% by weight to 90% by weight based on the weight of the liquid crystal composition.

8. The liquid crystal composition according to claim 1, further containing at least one compound represented by formula (3) as a third component:

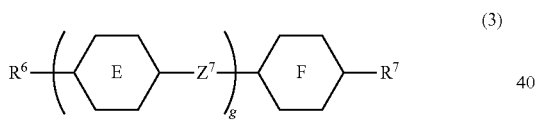

(3)

wherein, in formula (3), $R^6$ and $R^7$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring E and ring F are independently 1,4-cyclohexylene, 1,4-phenylene, 2-fluoro-1,4-phenylene or 2,5-difluoro-1,4-phenylene; $Z^7$ is a single bond, —CH$_2$CH$_2$—, —CH$_2$O—, —OCH$_2$—, —COO— or —OCO—; and g is 1, 2 or 3.

9. The liquid crystal composition according to claim 8, containing at least one compound selected from the group of compounds represented by formulas (3-1) to (3-13) as the third component:

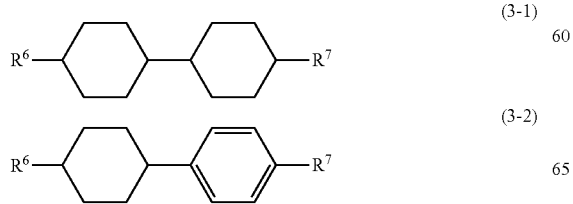

(3-1)

(3-2)

54

-continued

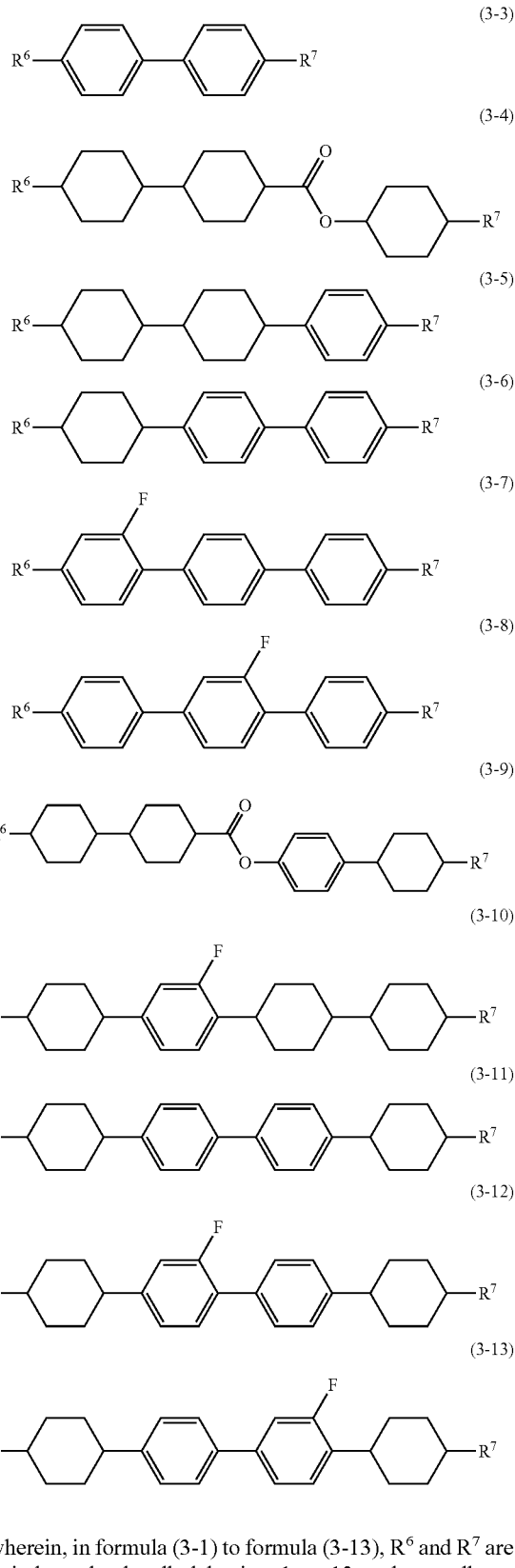

(3-3)

(3-4)

(3-5)

(3-6)

(3-7)

(3-8)

(3-9)

(3-10)

(3-11)

(3-12)

(3-13)

wherein, in formula (3-1) to formula (3-13), $R^6$ and $R^7$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

10. The liquid crystal composition according to claim 8, wherein a ratio of the third component is in the range of 10% by weight to 90% by weight based on the weight of the liquid crystal composition.

11. The liquid crystal composition according to claim 1, containing at least one polymerizable compound represented by formula (4) as an additive component:

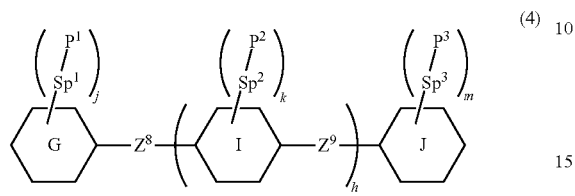
(4)

wherein, in formula (4), ring G and ring J are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; ring I is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen; $Z^8$ and $Z^9$ are independently a single bond or alkylene having 1 to 10 carbons, and in the alkylene, at least one of —CH$_2$— may be replaced by —O—, —CO—, —COO— or —OCO—, and at least one of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine; $P^1$, $P^2$ and $P^3$ are a polymerizable group; $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$—CH$_2$— may be replaced by —CH=CH— or —C≡C—, and in the groups, at least one of hydrogen may be replaced by fluorine or chlorine; h is 0, 1 or 2; and j, k and m are independently 0, 1, 2, 3 or 4, and a sum of j, k and m is 1 or more.

12. The liquid crystal composition according to claim 11, wherein in formula (4), $P^1$, $P^2$ and $P^3$ are independently a polymerizable group selected from the group of groups represented by formulas (P-1) to (P-5):

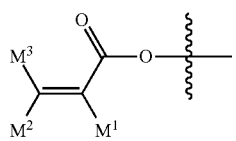
(P-1)

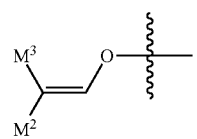
(P-2)

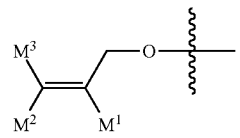
(P-3)

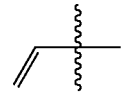
(P-4)

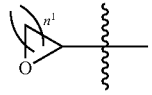
(P-5)

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (P-5), $n^1$ is 1, 2, 3 or 4; when both $P^1$ and $P^3$ are a group represented by formula (P-4), in formula (4), at least one of $Sp^1$ and $Sp^3$ is alkylene in which at least one of —CH$_2$— is replaced by —O—, —COO—, —OCO— or —OCOO—.

13. The liquid crystal composition according to claim 11, containing at least one polymerizable compound selected from the group of compounds represented by formulas (4-1) to (4-27) as the additive component:

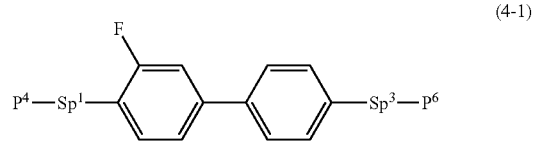
(4-1)

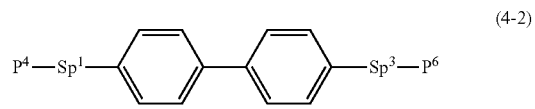
(4-2)

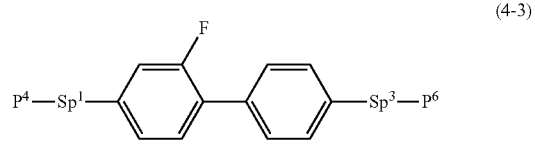
(4-3)

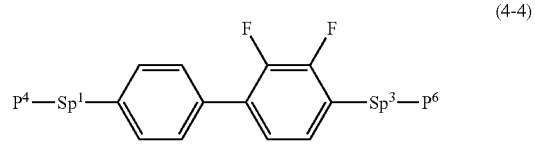
(4-4)

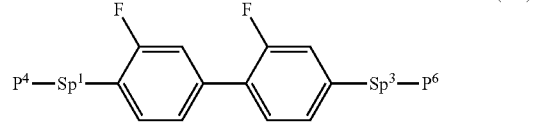
(4-5)

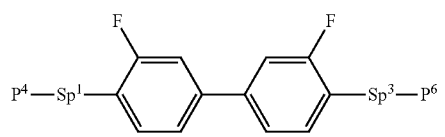 (4-6)
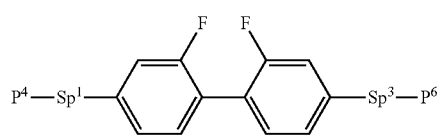 (4-7)
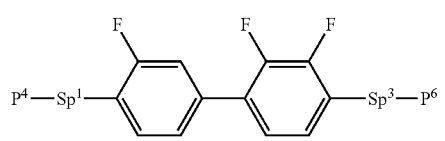 (4-8)
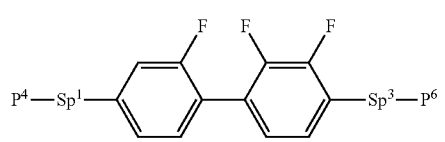 (4-9)
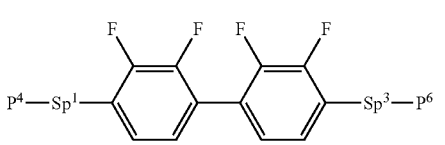 (4-10)
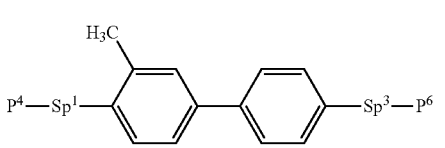 (4-11)
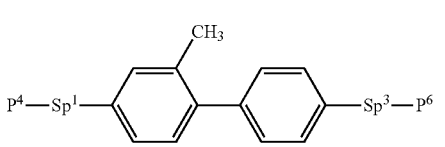 (4-12)
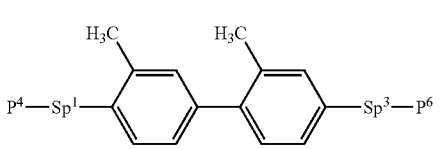 (4-13)
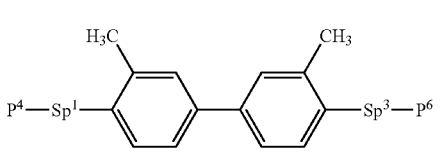 (4-14)
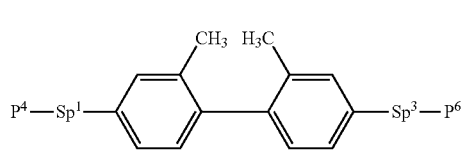 (4-15)
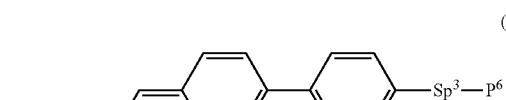 (4-16)
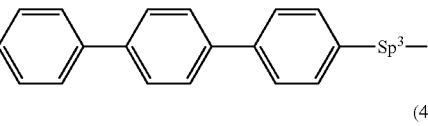 (4-17)
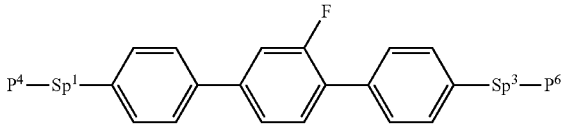 (4-18)
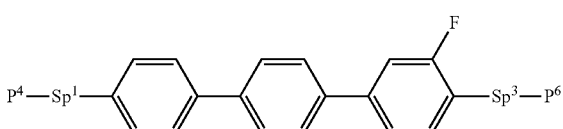 (4-19)
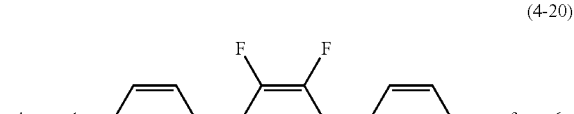 (4-20)
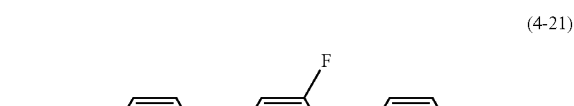 (4-21)
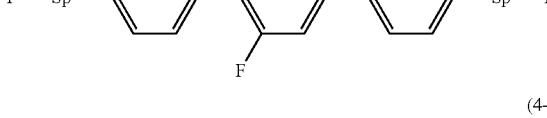 (4-22)
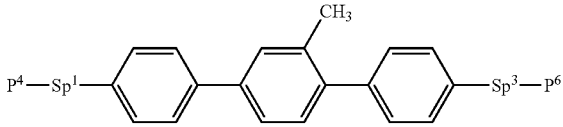 (4-23)
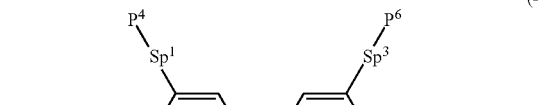 (4-24)
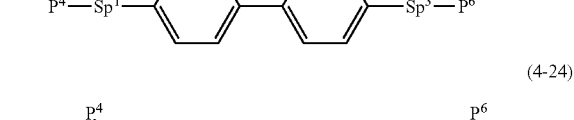 (4-25)
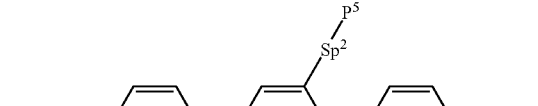
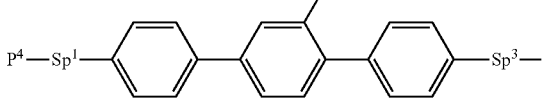

-continued (4-26)
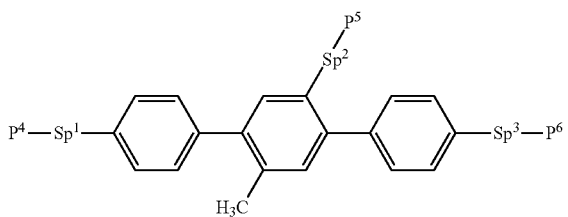

(4-27)
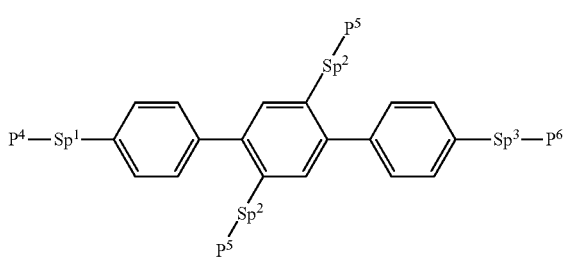

wherein, in formula (4-1) to formula (4-27), $P^4$, $P^5$ and $P^6$ are independently a group represented by formulas (P-1) to (P-3);

(P-1)
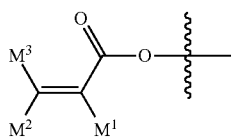

(P-2)
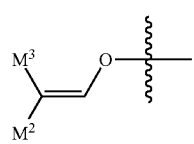

(P-3)
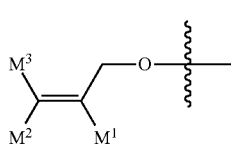

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by halogen; in formula (4-1) to formula (4-27), $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$—$CH_2$— may be replaced by —CH=CH— or —C≡C—, and in the groups, at least one of hydrogen may be replaced by fluorine or chlorine.

14. The liquid crystal composition according to claim 11, wherein a ratio of addition of the additive component is in the range of 0.03% by weight to 10% by weight, based on the weight of the liquid crystal composition before adding an additive thereto.

15. A liquid crystal display device, including the liquid crystal composition according to claim 1.

16. The liquid crystal display device according to claim 15, wherein an operating mode in the liquid crystal display device is an IPS mode, a VA mode, an FFS mode or an FPA mode, and a driving mode in the liquid crystal display device is an active matrix mode.

17. A polymer sustained alignment mode liquid crystal display device, wherein the liquid crystal display device includes the liquid crystal composition according to claim 11, and a polymerizable compound in the composition is polymerized.

18. The liquid crystal composition according to claim 5, further containing at least one compound represented by formula (3) as a third component:

(3)
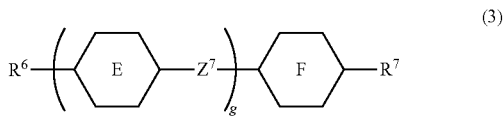

wherein, in formula (3), $R^6$ and $R^7$ are independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring E and ring F are independently 1,4-cyclohexylene, 1,4-phenylene, 2-fluoro-1,4-phenylene or 2,5-difluoro-1,4-phenylene; $Z^7$ is a single bond, —$CH_2CH_2$—, —$CH_2O$—, —$OCH_2$—, —COO— or —OCO—; and g is 1, 2 or 3.

\* \* \* \* \*